(12) United States Patent
Herrera et al.

(10) Patent No.: US 11,628,271 B2
(45) Date of Patent: Apr. 18, 2023

(54) URINARY CATHETER

(71) Applicant: Spinal Singularity, Inc., San Clemente, CA (US)

(72) Inventors: Derek Herrera, San Clemente, CA (US); Jeffery S. Kasalko, San Clemente, CA (US)

(73) Assignee: Spinal Singularity, Inc., San Clemente, CA (US)

( * ) Notice: Subject to any disclaimer, the term of this patent is extended or adjusted under 35 U.S.C. 154(b) by 286 days.

(21) Appl. No.: 16/436,773

(22) Filed: Jun. 10, 2019

(65) Prior Publication Data

US 2020/0384241 A1 Dec. 10, 2020

(51) Int. Cl.
  *A61M 25/00* (2006.01)
  *A61M 25/01* (2006.01)
  (Continued)

(52) U.S. Cl.
  CPC ...... *A61M 25/0017* (2013.01); *A61M 25/002* (2013.01); *A61M 25/0111* (2013.01);
  (Continued)

(58) Field of Classification Search
  CPC ............ A61M 25/0017; A61M 25/002; A61M 25/0111; A61M 25/04; A61M 2210/1085; A61M 2025/1004; A61M 27/002; A61M 25/10; A61M 25/1002; A61M 2025/1084; A61M 25/1038; A61F 5/451; A61B 5/1116; A61B 5/6882; A61B 5/002; A61B 5/01; A61B 5/14507; A61B 5/14539; A61B 5/14546; A61B 5/204; A61B 5/205;
  (Continued)

(56) References Cited

U.S. PATENT DOCUMENTS 3,630,206 A 12/1971 Gingold
3,713,447 A * 1/1973 Adair .................... A61M 25/04
                                                   604/105
(Continued)

FOREIGN PATENT DOCUMENTS

EP   1096900    9/2005
EP   2094343    10/2017
(Continued)

OTHER PUBLICATIONS

USPTO; Notice of Allowance dated Aug. 17, 2017 in U.S. Appl. No. 15/419,948.
(Continued)

*Primary Examiner* — Kai H Weng
*Assistant Examiner* — Brandon W. Levy
(74) *Attorney, Agent, or Firm* — Snell & Wilmer L.L.P.

(57) ABSTRACT

A urinary catheter is described that can be retained inside the body for extended periods. A catheter mating device can connect to the catheter to move the catheter inside of the body or remove it from the body. The catheter includes one or more of: (1) a retention portion having an outer cover, an inner cavity, and at least one structure in the inner cavity that exerts outward force on the outer cover, and (2) an extendable flap at the catheter's distal end. The retention portion and/or extendable flap each are configured to retain the catheter in the proper position inside of a user's body.

32 Claims, 24 Drawing Sheets

(51) Int. Cl.
*A61F 5/451* (2006.01)
*A61M 25/04* (2006.01)

(52) U.S. Cl.
CPC .............. *A61F 5/451* (2013.01); *A61M 25/04* (2013.01); *A61M 2210/1085* (2013.01)

(58) Field of Classification Search
CPC ..... A61B 5/686; A61B 5/6852; A61B 5/6874; A61B 2505/03; A61B 2017/3486
See application file for complete search history.

(56) References Cited

U.S. PATENT DOCUMENTS

| | | | |
|---|---|---|---|
| 3,812,841 A | | 5/1974 | Isaacson |
| 3,938,529 A | * | 2/1976 | Gibbons ............. A61M 27/008 604/524 |
| 4,043,346 A | * | 8/1977 | Mobley ................. A61M 25/04 606/198 |
| 4,168,699 A | | 9/1979 | Hauser |
| 4,710,169 A | | 12/1987 | Christopher |
| 4,932,938 A | | 6/1990 | Goldberg |
| 4,986,810 A | * | 1/1991 | Semrad ................. A61M 25/04 604/106 |
| 5,041,092 A | | 8/1991 | Barwick |
| 5,366,506 A | | 11/1994 | Davis |
| 5,380,268 A | | 1/1995 | Wheeler |
| 5,411,507 A | | 5/1995 | Heckele |
| 5,476,434 A | | 12/1995 | Kalb et al. |
| 5,628,770 A | | 5/1997 | Thome et al. |
| 5,713,877 A | | 2/1998 | Davis |
| 5,749,826 A | * | 5/1998 | Faulkner ............... A61M 25/04 600/29 |
| 6,053,897 A | | 4/2000 | Sachse |
| 6,066,088 A | | 5/2000 | Davis |
| 6,132,365 A | | 10/2000 | Sigurdsson |
| 6,167,886 B1 | | 1/2001 | Engel |
| 6,527,702 B2 | | 3/2003 | Whalen |
| 6,565,536 B1 | | 5/2003 | Sohn |
| 6,602,243 B2 | | 8/2003 | Noda |
| 6,638,208 B1 | | 10/2003 | Natarajan et al. |
| 6,835,183 B2 | | 12/2004 | Lennox et al. |
| 7,001,327 B2 | | 2/2006 | Whalen |
| 7,147,606 B1 | | 12/2006 | Chang et al. |
| 7,338,028 B2 | | 3/2008 | Zimmerling et al. |
| 7,415,308 B2 | | 8/2008 | Gerber et al. |
| 7,803,106 B2 | | 9/2010 | Whalen et al. |
| 8,801,697 B2 | | 8/2014 | Yugari |
| 8,882,652 B2 | | 11/2014 | Vitzthum |
| 9,011,314 B2 | | 4/2015 | Davis et al. |
| 9,452,278 B2 | | 9/2016 | Davis et al. |
| 9,775,698 B2 | | 10/2017 | Herrera et al. |
| 2002/0010476 A1 | | 1/2002 | Mulholland |
| 2002/0165427 A1 | | 11/2002 | Yachia et al. |
| 2002/0198506 A1 | | 12/2002 | Whalen |
| 2003/0167069 A1 | | 9/2003 | Gonzales |
| 2003/0208183 A1 | | 11/2003 | Whalen |
| 2003/0229263 A1 | | 12/2003 | Connors et al. |
| 2004/0019369 A1 | | 1/2004 | Duncan et al. |
| 2004/0068252 A1 | * | 4/2004 | Whitmore ......... A61M 25/0069 604/544 |
| 2004/0106899 A1 | | 6/2004 | McMichael et al. |
| 2005/0177102 A1 | | 8/2005 | Hart |
| 2005/0216069 A1 | | 9/2005 | Cohen et al. |
| 2006/0020297 A1 | | 1/2006 | Gerber |
| 2006/0184090 A1 | | 8/2006 | Davis et al. |
| 2006/0211946 A1 | | 9/2006 | Mange et al. |
| 2006/0247723 A1 | | 11/2006 | Gerber et al. |
| 2008/0269546 A1 | | 10/2008 | Wilkie et al. |
| 2008/0294069 A1 | | 11/2008 | Stickler et al. |
| 2009/0157053 A1 | | 6/2009 | Davis et al. |
| 2010/0234876 A1 | | 9/2010 | Watson |
| 2010/0312225 A1 | | 12/2010 | Armistead |
| 2011/0054404 A1 | | 3/2011 | Tanabe et al. |
| 2011/0066139 A1 | | 3/2011 | Winegar |
| 2012/0316584 A1 | | 12/2012 | Miles |
| 2013/0041430 A1 | | 2/2013 | Wang et al. |
| 2013/0090630 A1 | | 4/2013 | Winegar |
| 2014/0148648 A1 | | 5/2014 | Tycast et al. |
| 2014/0213979 A1 | | 7/2014 | Boyco et al. |
| 2014/0214009 A1 | | 7/2014 | Reyes |
| 2014/0371803 A1 | | 12/2014 | Grill et al. |
| 2015/0087896 A1 | | 3/2015 | Wei et al. |
| 2015/0250991 A1 | * | 9/2015 | Silvestro ............ A61B 17/3478 606/194 |
| 2015/0366462 A1 | | 12/2015 | Ramos et al. |
| 2016/0000641 A1 | | 1/2016 | Driscoll et al. |
| 2016/0279389 A1 | | 9/2016 | Rosenberg |
| 2016/0354193 A1 | | 12/2016 | McNab |
| 2017/0156838 A1 | | 6/2017 | Herrera |
| 2018/0036107 A1 | | 2/2018 | Herrera |
| 2018/0140799 A1 | | 5/2018 | Herrera |
| 2018/0153669 A1 | | 6/2018 | Herrera |
| 2018/0153670 A1 | | 6/2018 | Herrera |
| 2018/0153671 A1 | | 6/2018 | Herrera |

FOREIGN PATENT DOCUMENTS

| | | |
|---|---|---|
| EP | 3247309 | 11/2017 |
| WO | 2000002499 | 1/2000 |
| WO | 2001010358 | 2/2001 |
| WO | 2011032150 | 3/2011 |
| WO | 2016118943 | 7/2016 |
| WO | WO2017015351 | 1/2017 |
| WO | 2017172998 | 10/2017 |
| WO | 2018200643 | 11/2018 |
| WO | 2019068104 | 4/2019 |

OTHER PUBLICATIONS

USPTO; Final Office Action dated Jul. 13, 2017 in U.S. Appl. No. 15/419,948.
USPTO; Office Action dated Jun. 16, 2017 in U.S. Appl. No. 15/419,948.
USPTO; Restriction Requirement dated Mar. 23, 2017 in U.S. Appl. No. 15/419,948.
USPTO; Restriction Requirement dated Jul. 5, 2018 in U.S. Appl. No. 15/072,345.
USPTO; Non-Final Office Action dated Oct. 23, 2018 in U.S. Appl. No. 15/072,345.
USPTO; Final Office Action dated Mar. 25, 2019 in U.S. Appl. No. 15/072,345.
USPTO; Non-Final Office Action dated Aug. 26, 2019 in U.S. Appl. No. 15/877,228.
USPTO; Non-Final Office Action dated Sep. 12, 2019 in U.S. Appl. No. 15/785,405.
USPTO; Non-Final Office Action dated Sep. 13, 2019 in U.S. Appl. No. 15/072,345.
USPTO; Non-Final Office Action dated Sep. 13, 2019 in U.S. Appl. No. 15/785,403.
EPO; Extended Search Report and Written Opinion dated Jan. 2, 2018 in EP16740891.3.
EPO; Supplementary European Search Report dated Jan. 19, 2018 in EP16740891.3.
Mexico: Non-Final Office Action dated Jan. 26, 2018 in MX2017-009517.
AUIPO; Office Action dated Jul. 22, 2019 in Australian Application No. 2016209038.
PCT; International Search Report dated Jul. 28, 2016 in International Application No. PCT/US2016/014648.
PCT; International Preliminary Report on Patentability dated Jul. 25, 2017 in International Application No. PCT/US2016/014648.
PCT; Written Opinion dated Jul. 25, 2016 in International Application No. PCT/US2016/014648.
PCT; International Search Report dated Aug. 17, 2017 in International Application No. PCT/US2017/024862.
PCT; Written Opinion dated Aug. 17, 2017 in International Application No. PCT/US2017/024862.

(56) References Cited

OTHER PUBLICATIONS

PCT; International Preliminary Report on Patentability dated Oct. 2, 2018 in International Application No. PCT/US2017/024862.
PCT; International Search Report dated Jan. 28, 2019 in International Application No. PCT/US2018/053806.
PCT; Written Opinion dated Jan. 28, 2019 in International Application No. PCT/US2018/053806.
USPTO; Notice of Allowance dated Apr. 23, 2020 in the U.S. Appl. No. 15/877,228.
USPTO; Notice of Allowance dated Apr. 24, 2020 in the U.S. Appl. No. 15/785,398.
USPTO; Non-Final Office Action dated Jun. 4, 2020 in the U.S. Appl. No. 15/785,403.
USPTO; Final Office Action dated Oct. 9, 2020 in the U.S. Appl. No. 15/785,403.
USPTO; Non-Final Office Action dated Jun. 2, 2020 in the U.S. Appl. No. 15/785,405.
USPTO; Final Office Action dated Sep. 16, 2020 in the U.S. Appl. No. 15/785,405.
EP; First Office Action in the EP Application No. 16740891.3 dated Feb. 10, 2020.
GB; Examination Report in the GB Application No. GB1713519.5 dated Sep. 17, 2020.
AU; Examination Report No. 1 in the AU Application No. 2016209038 dated Jul. 22, 2019.
AU; Examination Report No. 2 in the AU Application No. 2016209038 dated Jul. 10, 2020.
AU; Notice of Allowance in the AU Application No. 2016209038 dated Jul. 21, 2020.
EP; Notice to Respond to Search in the EP Application No. 18792715.7 dated May 8, 2020.
EP; Supplemental Search Report in the EP Application No. 16740891.3 dated Dec. 18, 2017.
GB; First Examination Report in the GB Application No. GB1713519.5 dated Jun. 5, 2020.
GB; Second Examination Report in the GB Application No. GB1713519.5 dated Nov. 17, 2020.
IL; First Exam Report in the IL Application No. 005164IL dated Aug. 5, 2020.
PCT; Written Opinion dated Aug. 17, 2017 in the PCT Application No. PCT/US2017/024862.
PCT; International Search Report and Written Opinion in the PCT Application No. PCT/US2018/053806 dated Jan. 18, 2018.
PCT; International Search Report and Written Opinion in the PCT Application No. PCT/US2020/036859 dated Oct. 9, 2020.
USPTO; Restriction Requirement dated Aug. 2, 2019 in U.S. Appl. No. 15/721,096.
USPTO; Restriction Requirement dated Aug. 9, 2019 in U.S. Appl. No. 15/877,228.
USPTO; Final Office Action dated Dec. 6, 2019 in U.S. Appl. No. 15/877,228.
USPTO; Final Office Action dated Jan. 22, 2020 in U.S. Appl. No. 15/721,096.
USPTO; Final Office Action dated Jan. 30, 2020 in U.S. Appl. No. 15/785,403.
USPTO; Notice of Allowance dated Feb. 5, 2020 in U.S. Appl. No. 15/072,345.
USPTO; Final Office Action dated Feb. 12, 2020 in U.S. Appl. No. 15/785,405.
UK; Office Action dated Feb. 5, 2020 in UK. Application No. GB1713519.3.
USPTO; Non-Final Office Action dated Apr. 13, 2020 in U.S. Appl. No. 15/785,398.
USPTO; Non-Final Office Action dated Jan. 19, 2021 in the U.S. Appl. No. 15/785,403.
USPTO; Non-Final Office Action dated Jan. 8, 2021 in the U.S. Appl. No. 15/785,405.
USPTO; Notice of Allowance dated Apr. 15, 2021 in the U.S. Appl. No. 15/785,405.
PCT; International Search Report and Written Opinion in the PCT Application No. PCT/US2020/057429 dated Feb. 11, 2021.

* cited by examiner

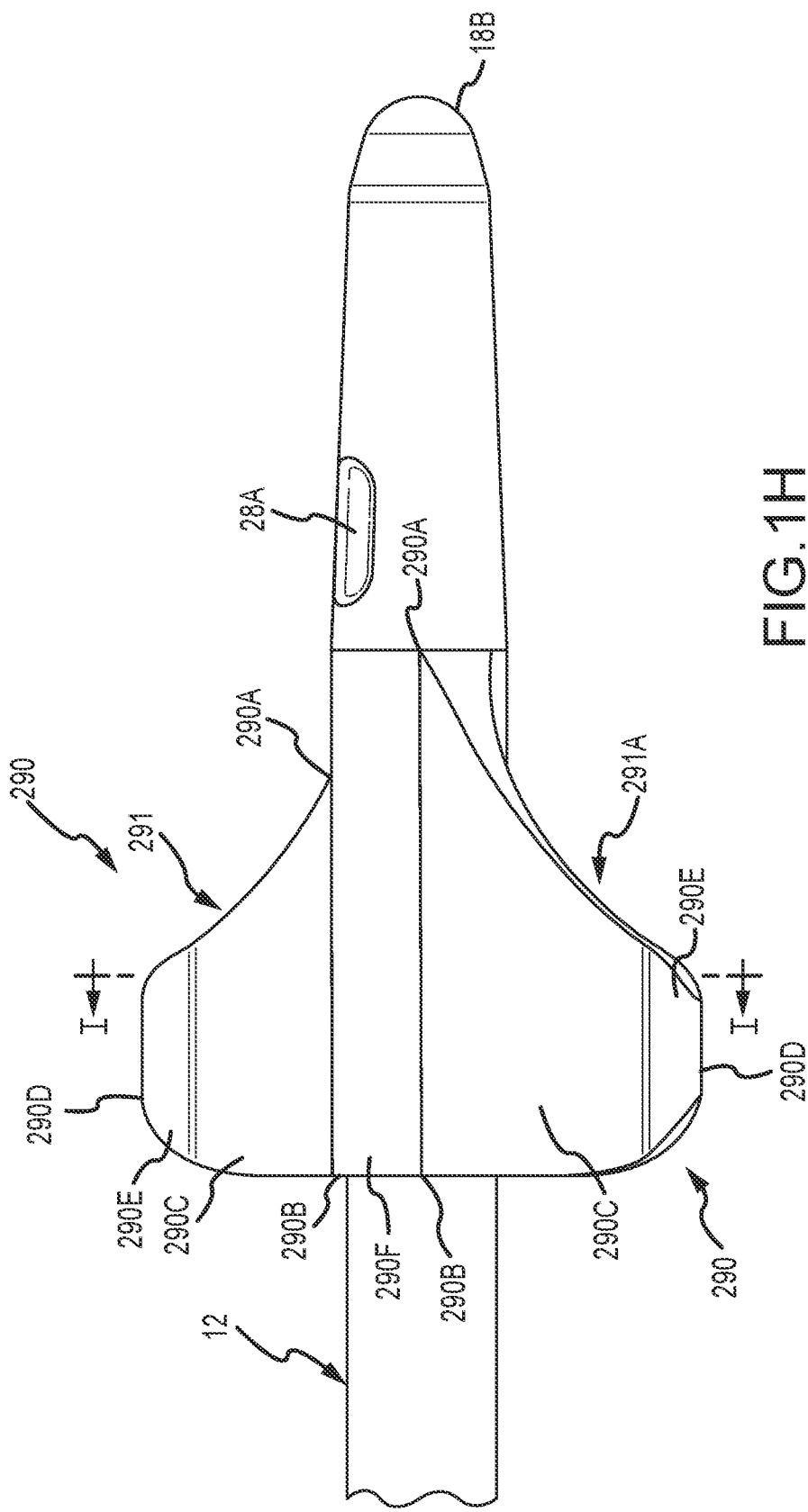

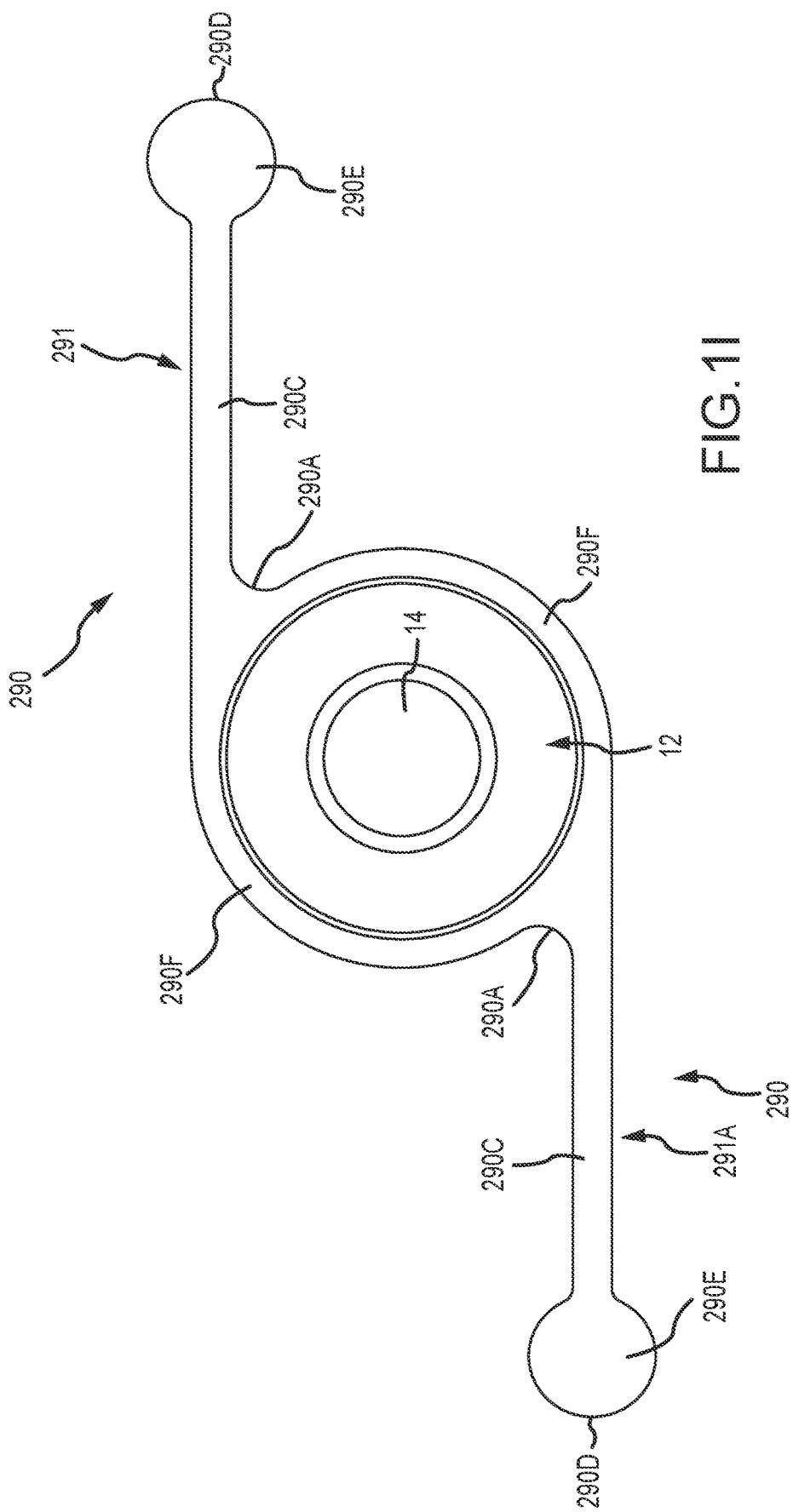

URINARY CATHETER

FIELD

This disclosure relates to an extended-use catheter with asymmetric retention features that enable it to be retained in the body for an extended time.

BACKGROUND

Many people suffer from lower urinary tract dysfunction, also known as neurogenic bladder. Neurogenic bladder can be defined as impaired urinary function due to neurological injury or disease, such as spinal cord injury (SCI). Some known methods for managing neurogenic bladder and other chronic urinary retention disorders are to drain the bladder using (a) intermittent catheterization (IC), or (b) indwelling Foley catheters. These methods, however, are associated with relatively high rates of urinary tract infection and genito-urinary (GU) injury, each of which diminishes a patient's quality of life. Furthermore, because some individuals with neurogenic bladder lack bladder sensation, and thus cannot accurately perceive bladder fullness, they are susceptible to bladder over-filling. This can result in urinary "accidents" and/or urinary reflux, and urinary reflux presents a risk of infection and tissue damage to the upper urinary tract.

To avoid these problems, individuals with neurogenic bladder on an IC program commonly rely on a timed catheterization schedule. This approach is imprecise and may lead to catheterization more frequently than necessary, which can increase the risk of infection and GU injury. Therefore, it is desirable to provide an improved urinary prosthesis that helps to alleviate one or all of the preceding problems.

This application incorporates by reference the following: U.S. application Ser. No. 15/072,345 to Herrera et al., entitled Extended-Use Valved Urinary Catheter, and filed on Mar. 16, 2016; PCT Application Serial No. PCT/US2016/014648, entitled Bladder Management Systems, and filed on Jan. 23, 2016; U.S. application Ser. No. 15/545,903 to Herrera et al., entitled Bladder Management System, and filed on Jul. 27, 2017; U.S. application Ser. No. 15/721,096 to Herrera et al., entitled Urinary Prosthesis Systems, and filed on Sep. 29, 2017; U.S. Pat. No. 9,775,698, entitled Urinary Prosthesis Systems; U.S. application Ser. No. 15/785,403 to Herrera, entitled Extended-Use Catheters, and filed on Oct. 16, 2017; U.S. Application Ser. No. 15/785,405 to Derek Herrera entitled Catheter Mating Devices, and filed on Oct. 16, 2017; U.S. application Ser. No. 15/785,398 to Derek Herrera entitled Catheters and Catheter Mating Devices and Systems, and filed on Oct. 16, 2017.

SUMMARY

The present disclosure relates to devices, systems and methods for extended-use bladder management and controlling urinary function for humans or other animals. The disclosed devices, systems, and methods may be used for fluid flow control for other bodily organs as well, such as kidneys, or draining abscesses or fluids from a body, and the description herein for bladder-control use is not limiting.

An extended-use catheter as disclosed is configured for being retained inside of the body. The catheter can be used, for example, in the human male or human female urinary tract. When in use, it is preferably positioned fully inside of, and retained in, the urethra and bladder. In one embodiment, the catheter comprises an elongated tube having a wall with an outer surface, and a lumen through which fluid, such as urine, can pass. Positioned on, or formed as part of, the tube wall is a retainer portion with a cross-sectional area greater than the cross-sectional area of the outer surface of the tube wall. The retainer portion has an outer wall, an inner cavity inside the outer wall, and at least one structure in the inner cavity that exerts outward force on the outer wall. At least one structure in the inner cavity may be wing shaped or of any suitable shape. The retainer portion can be compressed to a first, compressed position in which it is configured to fit through the penile urethra. When not compressed, the retainer portion has a second, expanded position in which it cannot fit through the penile urethra or the external urinary sphincter. The retainer portion can be moved from the second, expanded position to the first, compressed position by applying sufficient force to push it into, or pull it through, the penile urethra. In addition to the retention portion, or instead of the retention portion, the catheter may include an extendable flap at its distal end. The extendable flap has a first position in which it is against the outer surface of the catheter tube and can fit through the penile urethra. The extendable flap has a second, extended position in which it extends outward from the outer surface of the catheter tube and cannot pass through the penile urethra. The extendable flap can be moved from the second, extended position to the first position by applying sufficient pushing or pulling force to the proximal end of the catheter in order to push it into, or pull it through, the penile urethra.

When the catheter is properly positioned in the urinary tract, the retainer portion is positioned in the bulbar urethra, where it is in its second, expanded position and aids in the proper positioning of the catheter and helps prevent the catheter from inadvertently moving forward or backward. If the extendable flap is utilized, when the catheter is properly positioned in the urinary tract, the extendable flap may be positioned in the bladder or prostatic urethra and is in its second, extended position. In this position the extendable flap aids in the proper positioning of the catheter and helps prevent the catheter from inadvertently moving forward out of the urinary tract.

The catheter preferably includes a valve, wherein the valve can be operated to: (a) allow fluid to exit the proximal end of the catheter, where it can exit the body, or (b) prevent the flow of fluid out of the proximal end of the catheter. The valve is most preferably a magnetic valve controlled from outside of the body using a wireless controller that generates a wireless signal to the valve to open or close.

A catheter according to this disclosure could be periodically inserted, removed, and replaced by the user without medical assistance or the aid of another individual, which is convenient and saves time and medical expense. Such a catheter could remain in the body for days or weeks without being removed, which alleviates the problem of catheterization multiple times per day.

The catheter may be configured to include one or more sensors, which may be on, inside of, or embedded in material forming the catheter, or partially or entirely within the lumen. The one or more sensors can be at any suitable location on the catheter, such as at a position where they are positioned in the bladder when the catheter is properly positioned in the lower urinary tract of a human male. The one or more sensors could collect any relevant data, such as fluid pressure in the bladder, pH level of fluid, temperature, volume of urine in the bladder, and/or amount of blood or bacteria in urine. The one or more sensors could communicate with other devices, such as CT scanners, ultrasound devices, x-ray machines, electronic data storage devices, computers, cell phones, the wireless controller, the catheter mating device and/or sensors placed in toilets or hospital beds. The data collected by the sensors could be stored, analyzed and/or transmitted by a device including software configured for these functions.

Because the catheter can remain in the body for long periods, a sensor on the catheter can gather and send data over the entire period the catheter is in the body, as opposed to gathering data only at a specific time, such as when a patent is at a doctor's office or hospital.

A catheter according to aspects of the invention could also include one or more antennas to communicate with the one or more sensors, and transmit data collected by the one or more sensors. The catheter could have a second lumen that includes one or more antennas and one or more catheters and also may be co-extruded within the catheter itself.

A catheter mating device configured to engage and move the catheter is also disclosed and may be part of a system according to aspects of the invention. The catheter mating device has a distal end and a proximal end. The distal end is configured to connect to the proximal end of the catheter, and includes an apparatus moveable between: (a) a first position, wherein the apparatus is retracted, and (b) a second position, wherein the apparatus is expanded. When in the first position, the apparatus is configured to fit into the lumen (or a mating chamber of the catheter) at the proximal end of the catheter. Once placed in the lumen, the apparatus can be moved to its second position, wherein the apparatus expands until it presses against and engages the wall of the lumen (or inner wall of the mating chamber). That connects the catheter mating device to the catheter, and the catheter can then be pushed into, or removed from a body structure, such as a bladder and urethra by, respectively, pushing or pulling the catheter mating device. Thus, the catheter mating device can be used to: (a) accurately place the catheter inside of a body, and/or (b) remove the catheter from a body.

As used herein, the term "user" means any person able to insert and/or remove a catheter as disclosed herein, and includes a patient, doctor, caregiver, and nurse. "Patient" means a person that uses a catheter as disclosed herein in his/her body. "Lower urinary tract" refers collectively to the urinary bladder and urethra. "Extended use" means a catheter that can be used without having to remove it from the body more than once every two days or longer.

BRIEF DESCRIPTION OF THE DRAWINGS

FIG. 1H is side view of the urinary catheter of FIG. 1G.
FIG. 1I is a cross-sectional view of the urinary catheter of FIG. 1H taken through line I-I of FIG. 1H.

DETAILED DESCRIPTION OF PREFERRED EMBODIMENTS

Extended-Use Catheter

Figure 1:
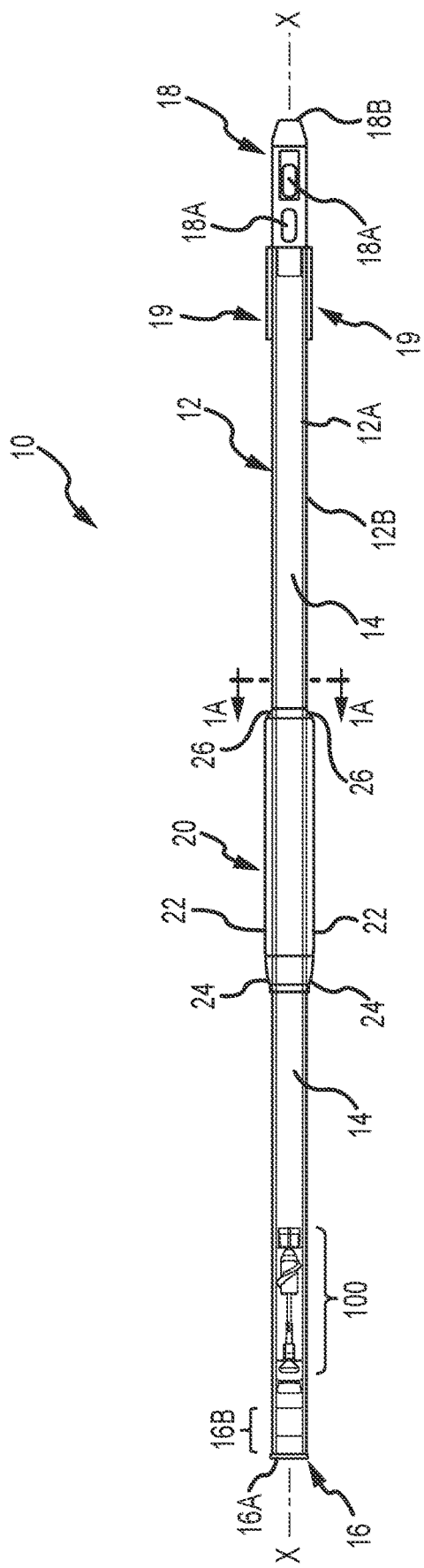
FIG. 1 is a side view of an exemplary urinary catheter.
Figure 2:
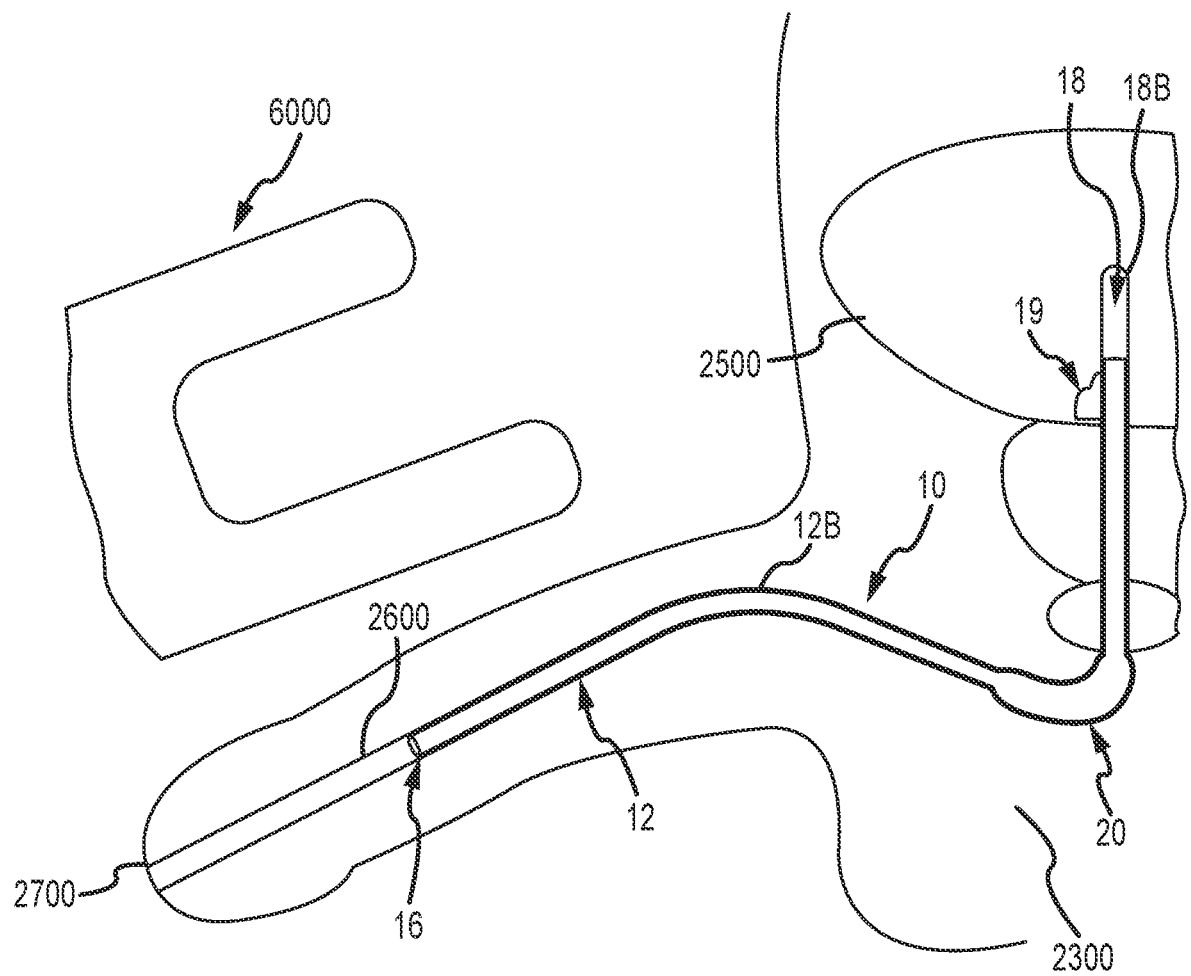
FIG. 2 shows the urinary catheter of FIGS. 1B-1E positioned in the lower urinary tract of a human male.
Figure 2A:
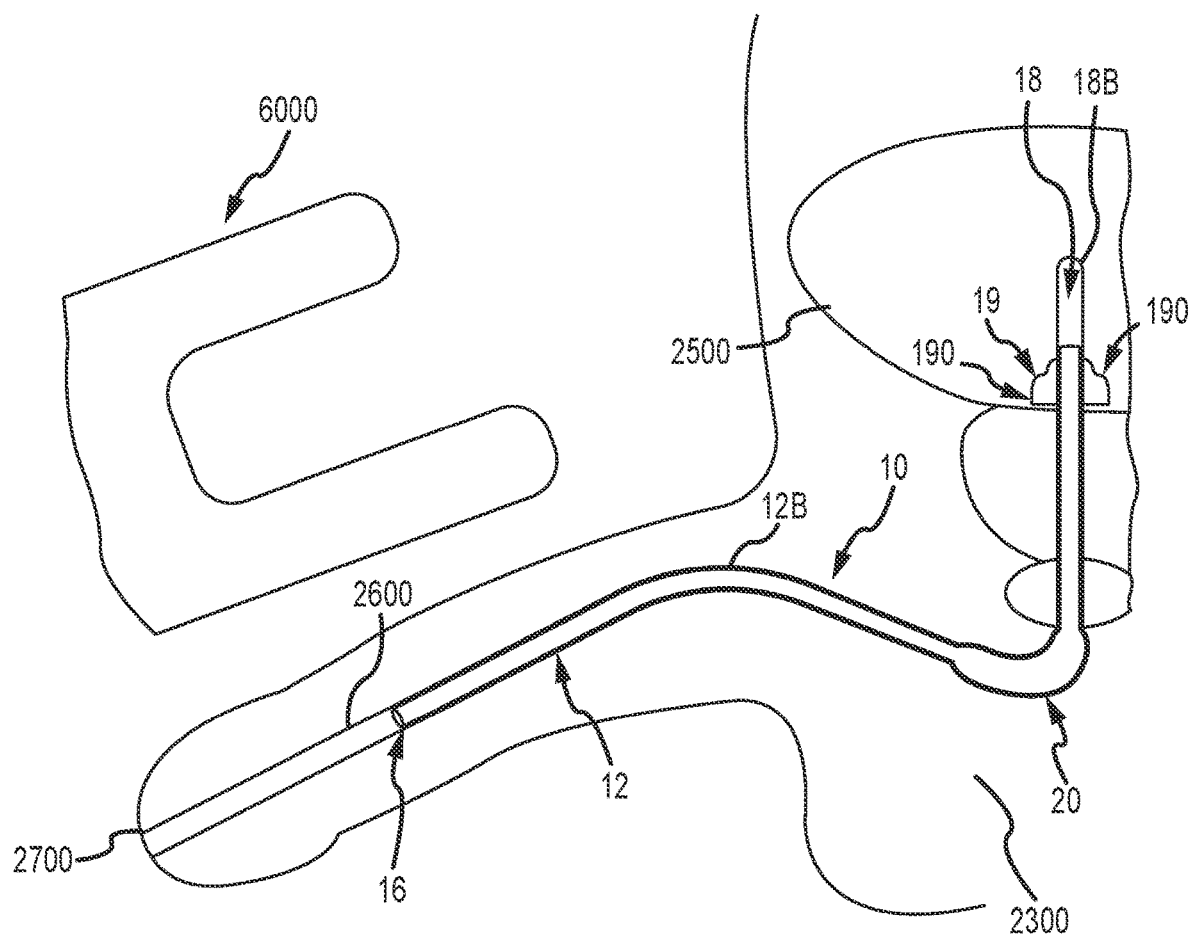
FIG. 2A shows the urinary catheter of FIGS. 1F-1I positioned in the lower urinary tract of a human male.

Turning now to the Figures, wherein the purpose is to describe preferred embodiments and not to limit the scope of the invention, FIG. 1 shows an exemplary catheter 10 according to aspects of the invention. Catheter 10 is an extended use catheter, and can be shaped and sized to be introduced into, and retained in, the lower urinary tract of a human male. As shown in FIG. 2, catheter 10 can extend from the bladder 2050 to a portion of the urethra 2600 distal to the prostate and distal to the bulbar urethra. Catheter 10 as shown in FIG. 2 extends past the prostate and the external urinary sphincter. In a female anatomy, the retainer portion is preferably positioned within the urethra, between the internal urethral orifice and the external urethral orifice. The retainer portion can then be positioned such that it is in the urethra between the meatus and the external urethral sphincter. Catheter 10 is preferably fully internal to the body once properly installed.

Figure 1A:
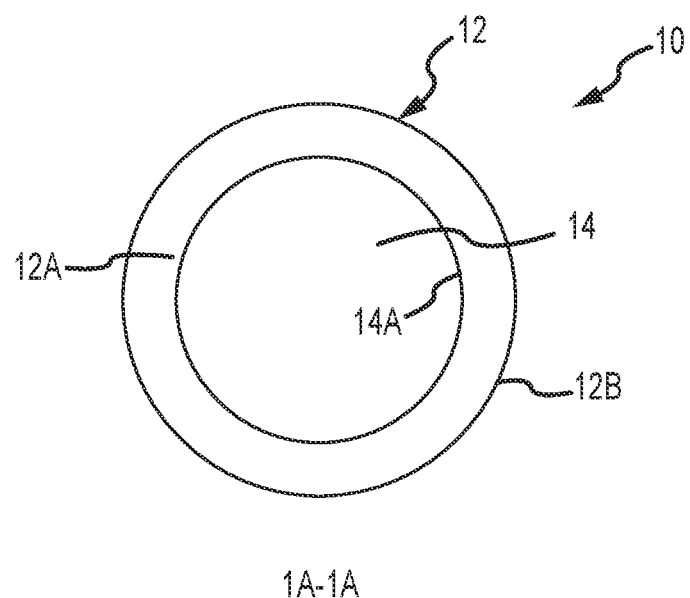
FIG. 1A is a cross-sectional view of the tube of the urinary catheter of FIG. 1 taken along lines 1A-1A.
Figure 1B:
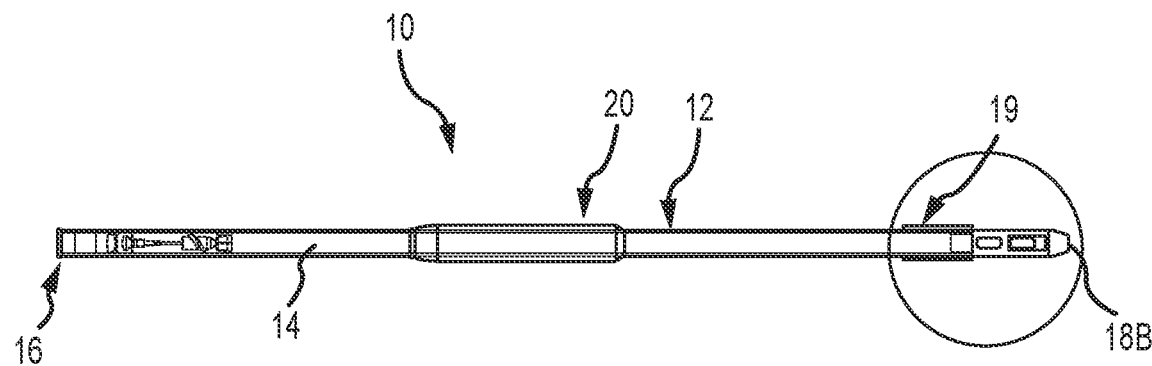
FIG. 1B is a side view of the urinary catheter of FIG. 1 with an extendable flap in its non-extended position.
Figure 1C:
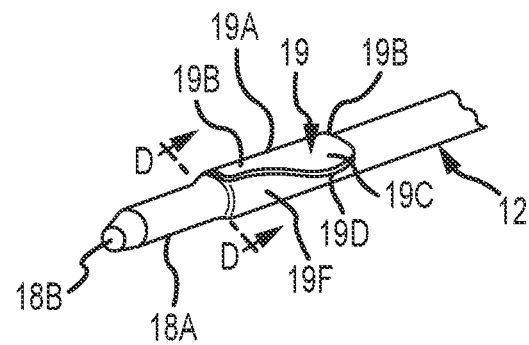
FIG. 1C is a rear, partial, perspective view of the urinary catheter of FIG. 1B with the flap extended.

Turning to FIGS. 1 and 1A, catheter 10 can comprise a tube 12 with a wall 12A having an outer surface 12B, a lumen 14 with a lumen wall 14A, a valve 100, a retainer portion 20, a proximal end 16 with a proximal tip 16A and an engagement chamber 16B, and a distal end 18 with openings 18A and a distal tip 18B. The catheter tube 12, which is shown in cross section in FIG. 1A, preferably has a circular cross-sectional shape, but can be of any shape suitable for the intended use of catheter 10. When used in the lower urinary tract of a human male, as shown in FIG. 2, tube 12 preferably has an outer diameter (as measured across outer surface 12B) ranging from about 1 French (0.3 mm) to 20 French (6.6 mm), which is approximately the same as or less than the maximum expanded dimension of the urethra 2600. Wall 12 can have a hardness of any amount from: about 30 Shore A to 55 Shore D, or about 60 Shore A, or about 30 to 70 Shore A, or about 20 to 50 Shore A, although any suitable hardness for the intended use of catheter 10 would suffice.

Lumen 14 may have any suitable cross-sectional geometrical shape (e.g., circular (which is most preferred), oval, semi-circular, rectangular, triangular, trapezoidal, or crescent) and can have a cross-sectional surface area (which is the area inside of lumen wall 14A when viewed in cross section) equivalent to the area of a 0.1 mm diameter circle to that of a 5.5 mm diameter circle. If the cross-sectional shape of lumen 14 is circular lumen 14 preferably has a diameter of any amount from: 0.1 mm to 5.5 mm. Lumen 14 may also comprise different cross-sectional areas along its length. For example, the cross-sectional area of the lumen may be greater where the valve 100 is positioned, and/or a greater cross-sectional area at the proximal end 16. Or, the lumen's cross-sectional area may be greater along its entire length distal to valve 100.

Tip 16A can have an outer diameter larger or smaller than the diameter of the outer wall 12B. For example, tip 16A may have a diameter of 0.5 mm-1 mm larger or smaller than outer wall 12B. The purpose of tip 16A having a slightly different diameter is so a user can locate it by touch (e.g., by pressing against the skin and feeling the ridge at tip 16A) when tip 16A is positioned in the penile urethra.

Figure 9:
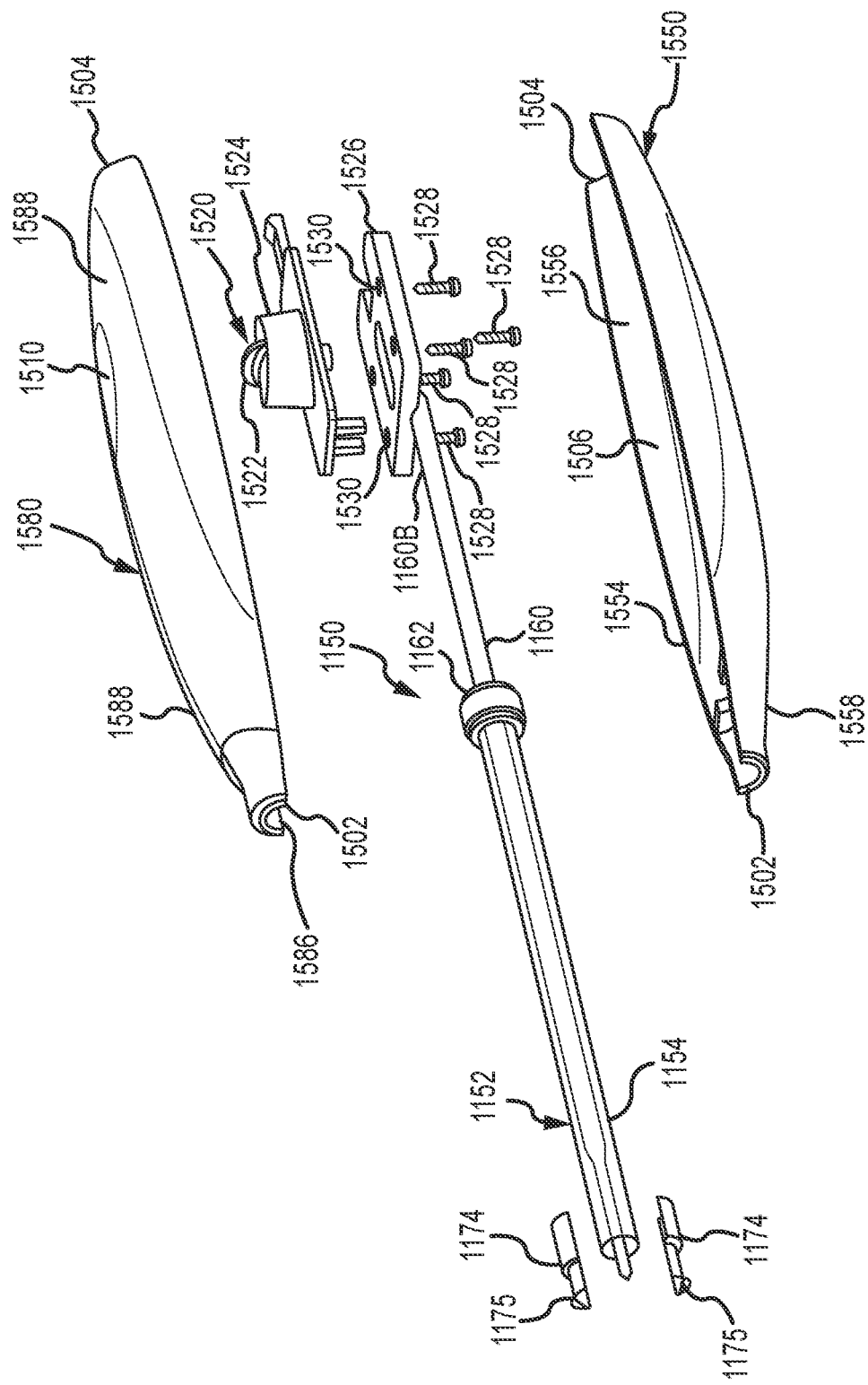
FIG. 9 is an exploded view of the catheter mating device of FIG. 8.
Figure 10:
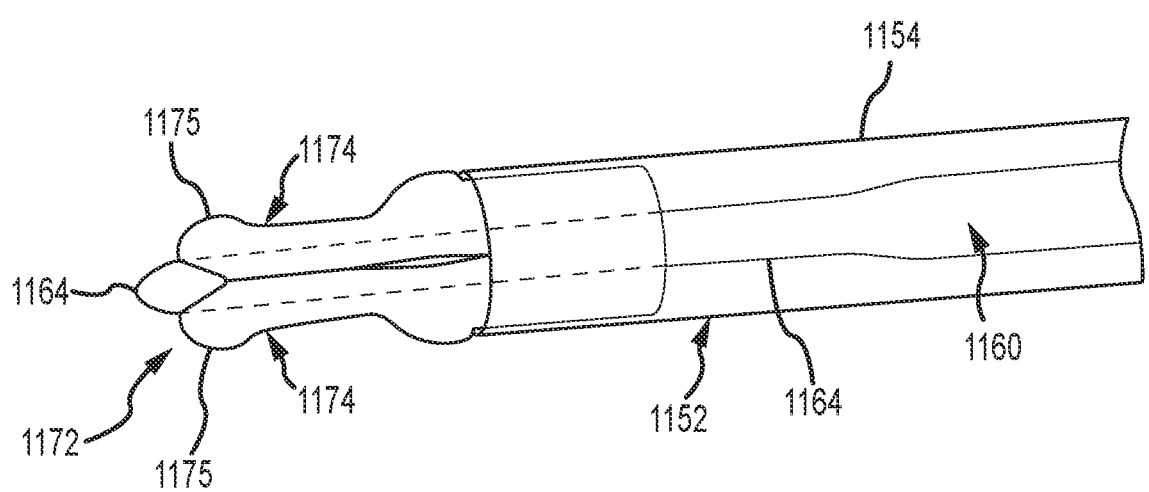
FIG. 10 is a side, perspective, close-up view of the distal end of the stem of the catheter mating device of FIG. 8.
Figure 11:
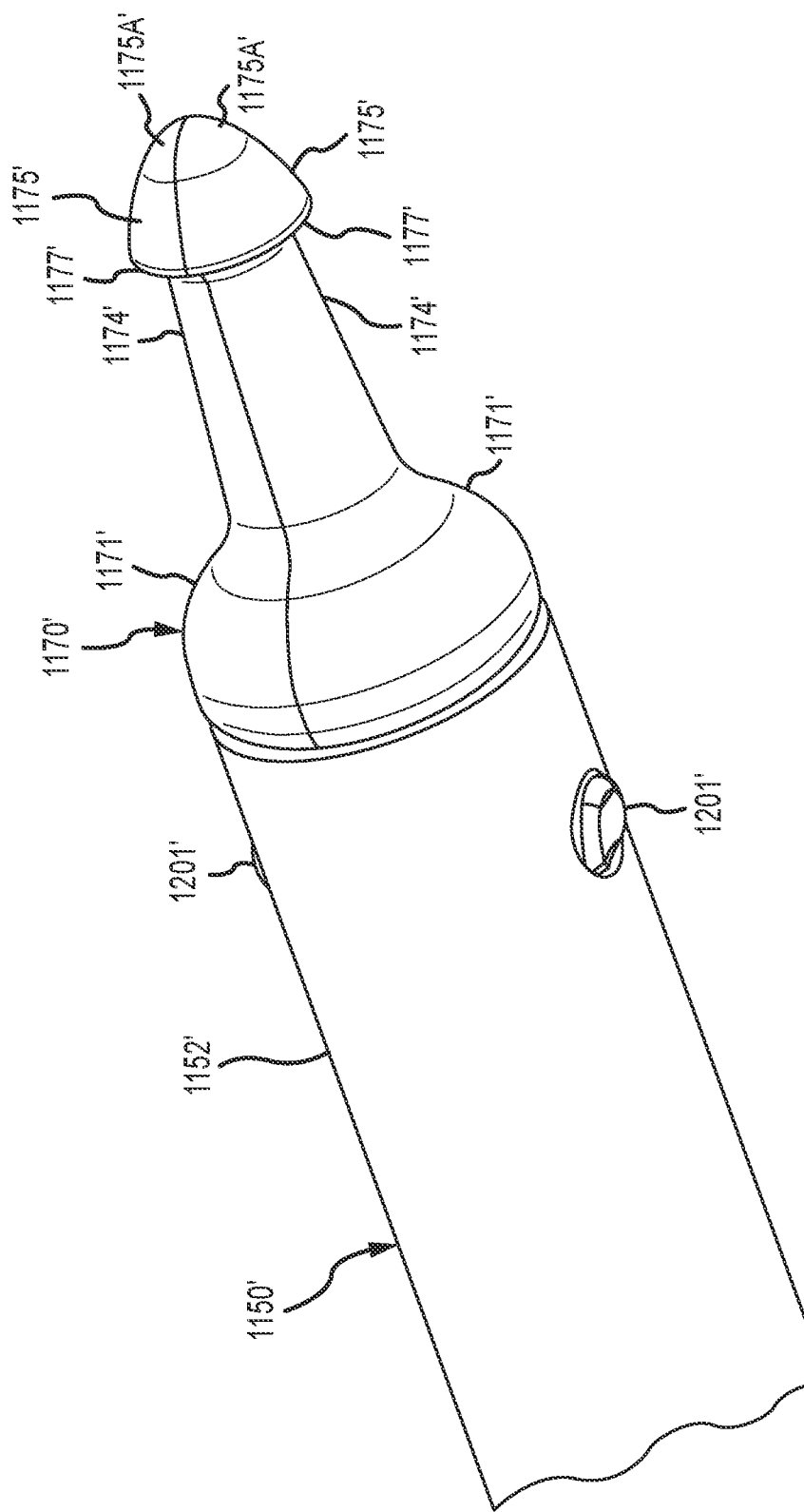
FIG. 11 is a partial, side perspective view of an alternate distal stem that may be used with a catheter mating device according to this disclosure.
Figure 12:
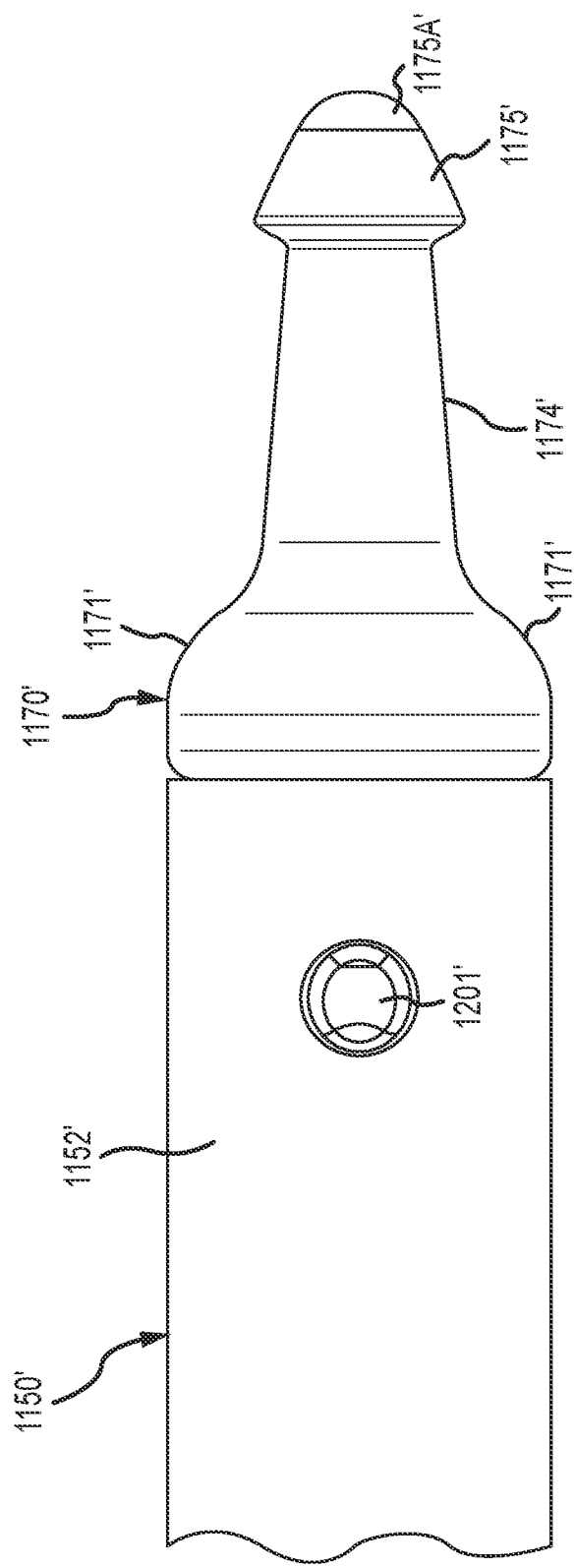
FIG. 12 is a partial, side view of the alternate distal end of FIG. 11.
Figure 13:
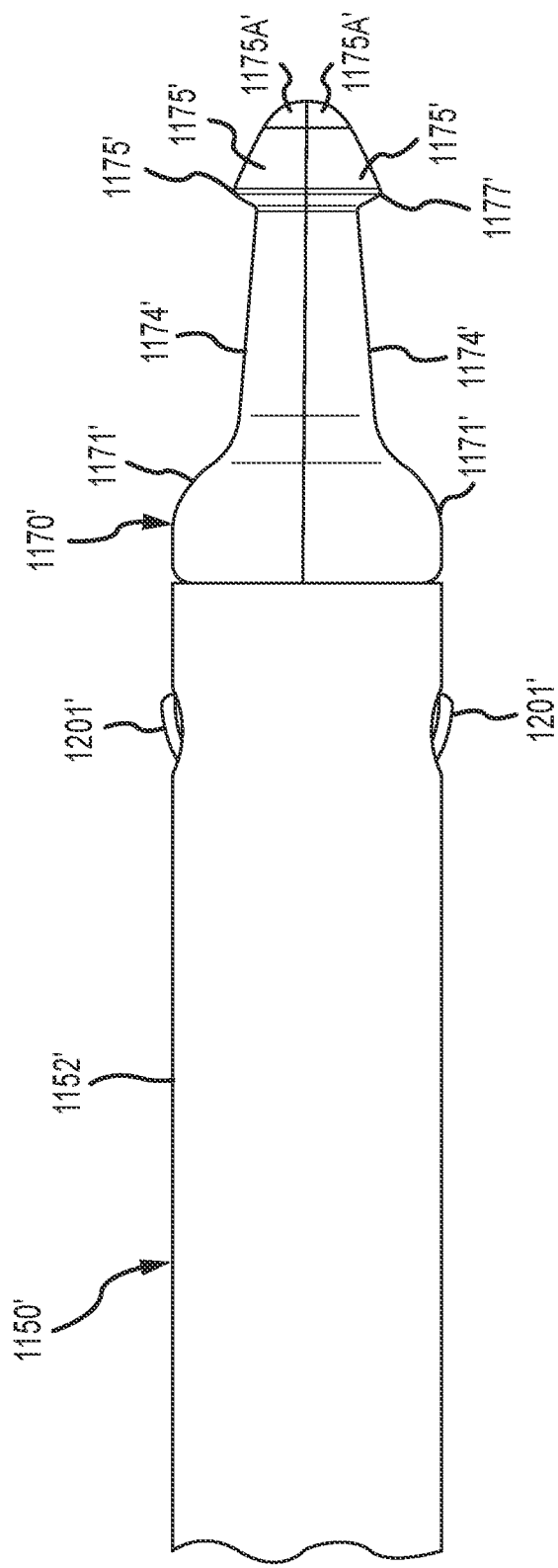
FIG. 13 is a partial, alternate side view of the alternate distal end of FIG. 11.
Figure 14:
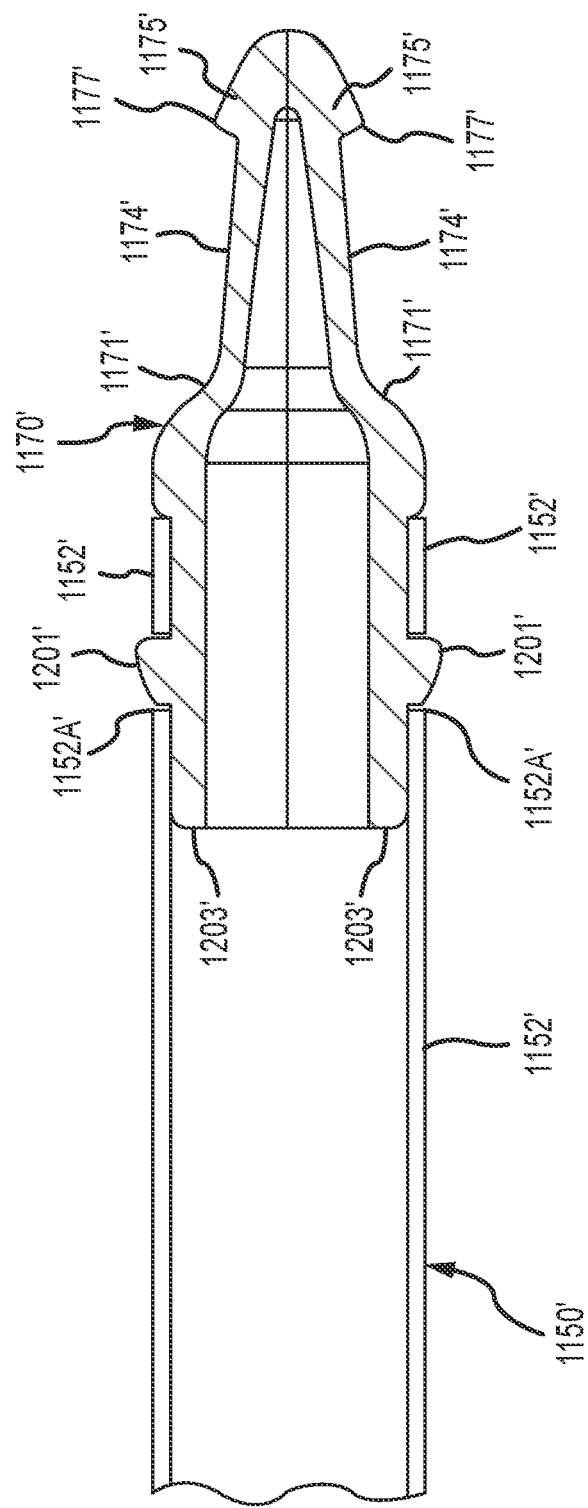
FIG. 14 is a partial, cross-sectional side view of the alternate distal end of FIG. 11.

An engagement chamber 16B can be at or near the proximal end 16 of the catheter 10. The engagement chamber 16B can be located between the proximal tip 16A and the valve 100, or extend from proximal tip 16A to valve 100 or a position proximal valve 100. The engagement chamber 16B includes a space configured to engage the apparatus 1172 as generally shown in FIGS. 9-11 and described below. The engagement chamber 16B can have an annular, cylindrical shape, with a circular cross-section although any suitable shape may be used. As shown, the engagement chamber 16B has a circular cross-sectional shape with a diameter preferably form 0.1 mm to 5.5 mm. The engagement chamber 16B may have a hardness greater than the hardness of tube 12. For example, the hardness may be of any hardness between 10 Shore A to 55 Shore D harder than tube 12, or 10 Shore A-20 Shore A harder, or 20 Shore A-50 Shore A harder, or 50 Shore A-55 Shore D harder. A purpose for engagement chamber 16B being harder than tube 12 is to better secure apparatus 1172 in engagement chamber 16B. It is not, however, required that catheter 10 have a mating chamber 16B. For example, apparatus 1172 could engage lumen wall 14A or another structure.

As shown in FIGS. 1 and 2, distal end 18 and tip 18B are configured to enter the patient's body through the urethral orifice 2700, and into the urethra 2600 when catheter 10 is positioned inside the lower urinary tract. As shown in this embodiment, distal tip 18B is tapered, rounded and closed. The distal tip 18B can comprise a material with hardness greater than the hardness of wall 12A. Distal end 18 permits the inflow of bodily fluid, such as urine, from a bladder or other body part into lumen 14, which can be accomplished in any suitable manner. One or more (as shown, two) openings 18A permit bodily fluid, such as urine, to enter lumen 14. As shown, openings 18A are on opposite sides of tube 12, so if one opening 18A is blocked because it is positioned against body tissue, the other opening 18A should still be unblocked. However, there need only be one opening, or there could be more than two openings, and the openings could be of any suitable size, configuration or location so they allow fluid, such as urine from the bladder, to enter lumen 14.

When catheter 10 is positioned in the lower urinary tract of a human male, the one or more openings 18A are positioned in the bladder 2500, as shown in FIG. 2.

Retainer Portion

The retainer portion 20 is positioned in the bulbar urethra 2300 when catheter 10 is properly positioned in the lower urinary tract of a human male. Retainer portion 20 is configured to prevent the inadvertent migration of catheter 10 either forward or backward once catheter 10 is properly positioned in the body. If positioned in the bulbar urethra, the retainer portion 20 is blocked by the external sphincter to prevent inadvertent retrograde migration, and blocked by the penile portion of the urethra 2600 to prevent inadvertent ante grade migration. When sufficient pulling or pushing force is applied to catheter 10, retainer portion 20 compresses from its second, expanded position to its first, compressed position so that it can pass through the penile portion of the urethra 2600. In this manner, catheter 10 can be removed from, or being placed in, the lower urinary tract.

Figure 3:
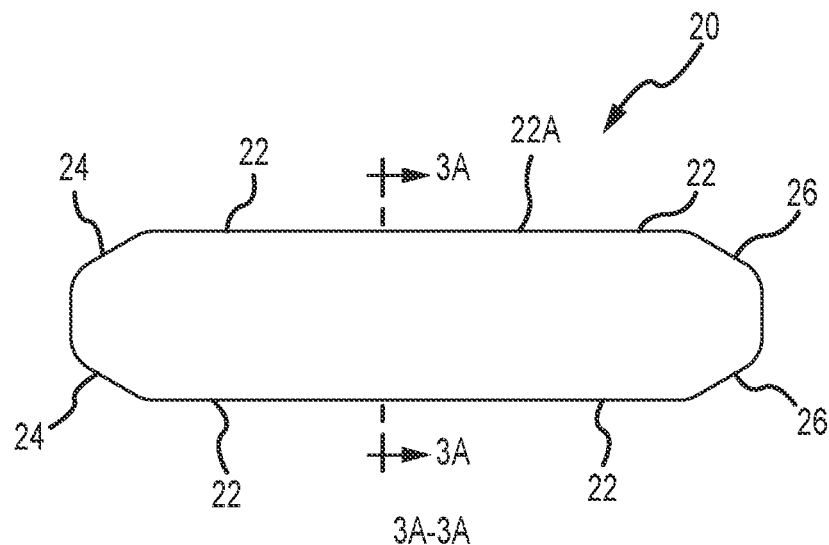
FIG. 3 is a side view of an exemplary embodiment of a urinary catheter retainer portion according to aspects of the invention.
Figure 3A:
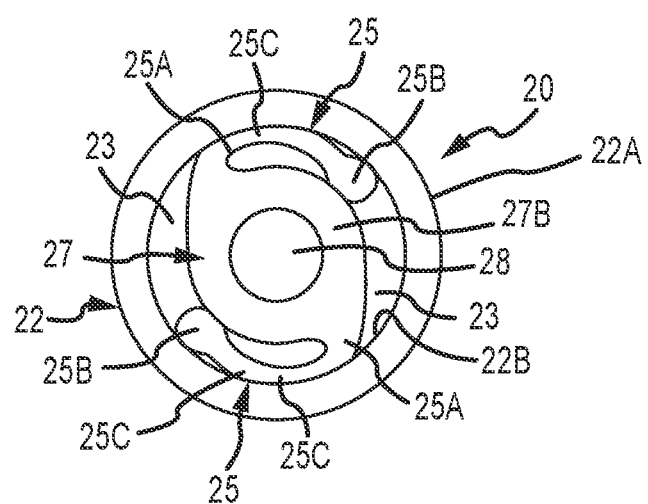
FIG. 3A is a cross-sectional view of the retainer portion of FIG. 3A taken along lines 3A-3A.
Figure 3B:
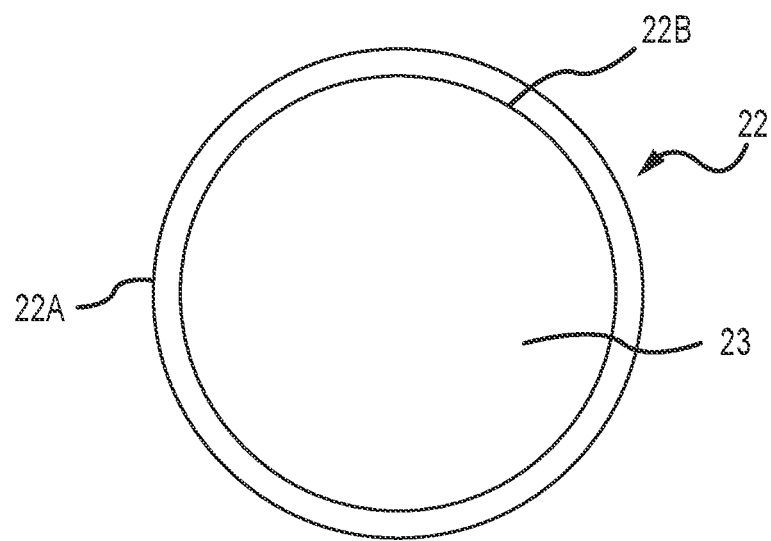
FIG. 3B is a cross-sectional view of the outer wall of the retainer portion of FIG. 3 taken along lines 3A-3A.
Figure 3C:
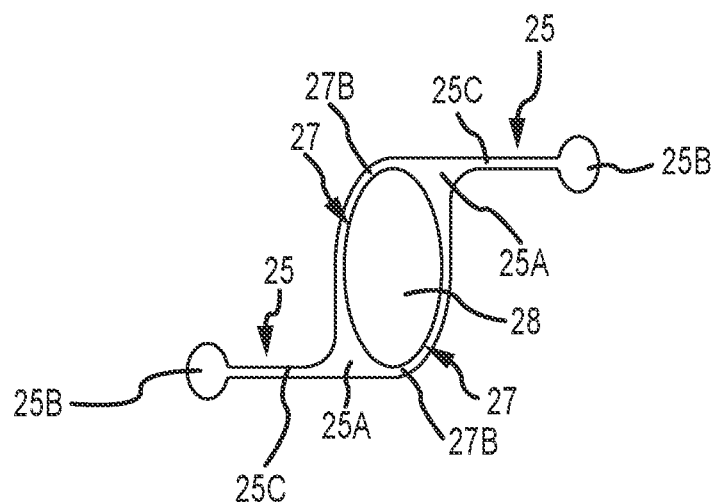
FIG. 3C is a cross-sectional view of the expansion structure shown in FIG. 3A.

Retainer portion 20 is positioned between the distal end 18 and the proximal end 10. Turning to FIGS. 3-3C, in the embodiment shown, retainer portion 20 has (1) an outer wall 22 that has an outer surface 22A, (2) an inner surface 22B, (3) a first, compressed position in which it is configured to fit through the penile urethra, and (4) a second, expanded position in which it has a maximum cross-sectional area measured around the outer surface 22A that is at least 30% greater than the first cross-sectional area of catheter tube 12. When in the second, expanded position, retainer portion 20 is configured so that it cannot fit through the penile urethra 2600. The retainer portion 20 is configured to have a maximum diameter of 0.3 mm to 8.0 mm when in the first, compressed position, and is configured to have a maximum diameter of 4.0 mm to 20 mm when in the second, expanded position. Retainer portion 20 has a cavity 23 inside of the outer wall 22.

An internal structure inside of the cavity 23 includes a core 27 and at least one expansion structure 25. The core 27 has a passage 28, in which the tube 12 is positioned, and a wall 27B. As shown, the at least one expansion structure 25 is connected to wall 27B of core 27, extends therefrom, and is configured to contact inner surface 22B of the outer wall 22 and exert outward force on the outer wall 22 to urge it towards its second, expanded position.

In the embodiment shown, the internal structure comprising core 27 and at least one expansion structure 25 is a single piece made in any suitable manner, such as by molding, over-molding, or extruding. In this embodiment, the inner structure is not formed with outer wall 22, but is formed separately and outer wall 22 is positioned over it. For example, tube 12 can be positioned inside of passage 28 of core 27, and then outer cover 22 can be positioned over tube 12 and expansion structure 25.

The retainer portion 20 as shown comprises two expansion structures 25 in the cavity 23 and each expansion structure 25 is configured to apply outward force on the outer cover 22. As shown, each expansion structure 25 is wing shaped and extends outward from the core 27. Each expansion structure 25 has a first end 25A connected to, or integrally formed with, the core 27 and a second end 25B that terminates in an enlarged sphere 25B. Each expansion structure 25 has an intermediate section 25C that touches inner wall 22B of the outer cover 22 in order to apply outward pressure.

Each expansion structure 25 has a length (as measured from first end 25A to second end 25B) that is at least 30%, at least 40%, or at least 50% of the circumference of the inner wall 25B of the outer cover 22, or has a length that is greater than 50% of the circumference of the inner wall 22B of the outer cover 22, such as at least 60%, or at least 70%, or at least 80% of the circumference.

Each expansion structure 25 has an intermediate section 25C having a thickness that is 25% or more, or 30% or more, or 40% or more of the thickness of the wall of outer cover 22 (i.e., the thickness as measured between outer wall 22A and inner wall 22B).

The outer wall 22 of the retainer portion 20 can be physically compressed to ½ or less of the maximum cross-sectional area when subjected to a compressive force evenly applied along the outer wall 22 of an amount from: 1-5 lbs., or 2-4 lbs., or 2-6 lbs., or 4-6 lbs., or 5-10 lbs., or 7-10 lbs., or 5-22 lbs.

Or, the outer wall 22 can be compressed from the second, expanded position to the first, compressed position, when the outer wall 22 is subjected to a compressive force evenly applied along the outer wall 22 of an amount from: 1-5 lbs., or 2-4 lbs., or 2-6 lbs., or 4-6 lbs., or 5-10 lbs., or 7-10 lbs., or 5-22 lbs.

Outer cover 22 of retainer portion 20 can comprise ribs, dimples, staples, or other structures on its outer surface to help retain it in the bulbar urethra or other body area.

As best seen in FIGS. 1 and 3, the retainer portion 20 can comprise an outer surface 22A, proximal tapered surface 24, and a distal tapered surface 26. The proximal tapered surface 24 can be tapered from the outer surface 22A to about the outer surface 12B of tube 12. The distal tapered surface 26 can be tapered from the outer surface 22A to about the outer surface 12A of tube 12. The retainer portion has a length as measured along the longitudinal axis X of catheter 10. In one embodiment the retainer portion 20 has a total length of any amount from about: 1 cm to 10 cm, or 2 cm to 8 cm, or 3 cm to 7 cm, or 4 cm to 6 cm, and top surface 22 has a length of any amount from about: 1 cm to 10 cm, or about 10%, about 20%, about 30%, or about 40%, or about 50%, or about 60%, or about 70%, or about 80%, or about 90%, or about 95%, or any amount from about 5% to 95%, of the total length of retainer portion 20.

In one exemplary embodiment, the overall length of retainer portion 20 is about 40 mm, the overall uncompressed width at its center is about 22 mm, the thickness of wall is about 0.75 mm, or any thickness between about 0.70 and 0.90 mm, or about 0.75 to 0.85 mm, and the radius of end 25B is about 2.0 mm, or any amount from about 0.5 mm and 2.1 mm.

In an embodiment suitable for use in the lower urinary tract of a human male, the maximum cross-sectional area as measured inside of outer surface 22A (and including the cross-sectional area of passage 28) is: (a) greater than the cross-sectional area of the external sphincter, (b) greater than the cross-sectional area of the penile urethra 2600, and (c) smaller than the cross-sectional dimension of the bulbar urethra 2300. The maximum cross-sectional area (as measured when retainer portion 20 is in its second, expanded position) may be 1.2 times larger, 1.5 to two times larger, three times as large, four times as large, five times as large, six times as large, seven times as large, eight times as large, nine times as large, ten times as large, or any amount from: 1.2 to five times as large, or 1.5 to ten times as large, as the cross-sectional area measured inside the outer surface 12B of tube 12. The maximum cross-sectional area (as measured when retainer portion 20 is not being compressed) may be any amount from: $(24 \text{ mm})^2 \pi$ to $(25 \text{ mm})^2 \pi$, $(4 \text{ mm})^2 \pi$ to $(25 \text{ mm})^2 \pi$, or $(6 \text{ mm})^2 \pi$ to $(20 \text{ mm})^2 \pi$, or $(8 \text{ mm})^2 \pi$ to $(16 \text{ mm})^2 \pi$, or $(10 \text{ mm})^2 \pi$ to $(15 \text{ mm})^2 \pi$, or $(12 \text{ mm})^2 \pi$ to $(15 \text{ mm})^2 \pi$, or $(5 \text{ mm})^2 \pi$ to $(10 \text{ mm})^2 \pi$. In one embodiment the outer surface 22A has a circular cross-sectional shape and has a diameter of any amount from: 5 mm to 10 mm, or 5 mm to 7 mm, or 4 mm to 8 mm, or 6 mm to 15 mm, or 8 mm to 15 mm, or 6 mm to 20 mm, or 8 mm to 22 mm. The diameter of surface 12B (which is the outer diameter of tube 12) can be about 2.0 mm to 6.0 mm, or 4.6 to 6.0 mm, or any amount from: 1.5 mm to 6.5 mm.

Example 1

The retention feature of a catheter as disclosed herein was quantitatively compared by assessing tensile forces utilizing a calibrated force gauge (E-00002, calibration due date: 30 Nov. 2019) while the catheter was pulled through a silicone model. The catheter designs were pulled in a forward direction (approximating removal) and in a reverse direction (approximating insertion and inward migration).

The silicone test model was manufactured with a variable inner diameter to approximate different portions of the urethra (the penile urethra, bulbous urethra and external sphincter). The model was molded in multiple silicone layers consisting of low durometer silicone and silicone gel to create a highly compliant inner diameter. The model was lubricated throughout the test using mineral oil to keep frictional forces as low as possible.

The average retention force of a catheter (after it has been properly positioned in the bladder of an adult, human male) according to this disclosure in the forward direction (i.e., into the bladder) was about: (1) 1.15 lbs. to 1.5 lbs., or about 1.15 lbs. and 1.70 lbs. The average retention force of a catheter (after it has been properly positioned in the bladder of an adult, human male) according to this disclosure in the reverse direction (i.e., outward from the bladder) was about: 1.30 lbs. to about 2.0 lbs., or about 1.3 lbs. to about 2.0 lbs., or about 1.3 lbs. to about 1.8 lbs.

In alternate embodiments, the catheter 10 may comprise two or more retainer portions 20A as shown in FIG. 3C for catheter 10', or have any suitable number of retainer portions along wall 12, wherein the plurality of retainer portions could be of different shapes and/or sizes. For example, the catheter 10 can comprise a first retainer portion 20A and a second retainer portion 20A, wherein (if catheter 10 is being used in the lower urinary tract of a human male) both are positioned in the bulbar urethra when catheter 10 is positioned in a body. Retainer portions 20A would have respective lengths suitable for fitting into a body area such as the bulbar urethra, for their intended use.

Figure 4:
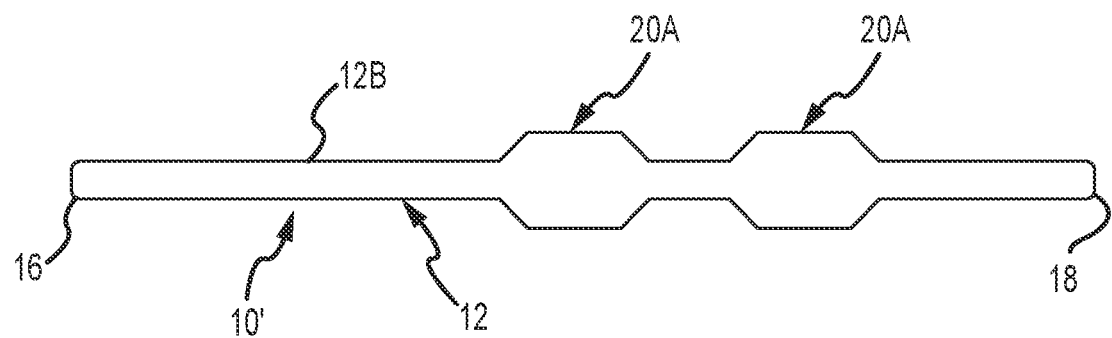
FIG. 4 is a side, perspective view of an alternative exemplary embodiment of a urinary catheter according to aspects of the invention that has a plurality of retainer portions.

FIG. 4 shows a catheter 10B that has a plurality of retainer portions 21, 21A, 21B, and 21C of different shapes and sizes. The retainer portions would have suitable shapes and sizes for fitting into one or more body areas, such as the bulbar urethra.

Regardless of the structure or number of the retainer portion(s) utilized, any retainer portion can be comprised of solid material, include gas pockets, or include an inner structure having at least one expansion structure, such as the ones described herein. Each retainer portion should be atraumatic, and it preferably has a relatively soft, atraumatic surface. Retainer portion can be comprised of a flexible silicone and/or have a soft silicone surface coating. The retainer portion preferably has a durometer of any amount from: 1 to 70, or 5 to 60, or 10 to 25, or 35-70 Shore A. The retainer portion is preferably compressible. For example, the retainer portion can comprise a material that compresses to pass through cross-sectional areas smaller than the maximum cross-sectional area of the retainer portion. When used in the lower urinary tract of a human male, the retainer portion should compress to at least a dimension so that it can be pushed or pulled through the maximum expanded dimension of urethra 2600, which could be about 6 mm to 12 mm, or about 10 mm. The retainer portion expands once it is no longer restricted. When used in the lower urinary tract of a human male, the retainer portion is compressed when it is pulled through the urethra 2600 and expands once it enters the bulbar urethra 2300.

In some embodiments, the retainer portion may be compressed to about 80%, 75%, 70%, 60%, 50%, 40%, 30%, 25%, 20%, 10%, or any amount from about 10%-80% of the maximum cross-sectional area. The retainer portion 20 is compressed to any such amount when a total force is applied substantially equally to the outer surface of the retainer portion at the maximum cross-sectional area in an amount of 2 lbs., 3 lbs., 4 lbs., 5 lbs., 6 lbs., 7 lbs., 8 lbs., 9 lbs., 10 lbs., 11 lbs., 12 lbs., 13 lbs., 14 lbs., 15 lbs., 16 lbs., 17 lbs., 18 lbs., 19 lbs., 20 lbs., or any force within the range of: 1-10 lbs., 2-20 lbs., or 0.5-5.0 lbs.

Extendable Flap

The urinary catheter may comprise an extendable flap 19 on the distal end 18, as shown in FIGS. 1B-1E and 2. The extendable flap 19 has a first, contracted position in which it is positioned against the outer surface 12B of tube 12, and a second, extended position (shown in FIGS. 1B to 1E) in which it extends outward from the outer surface 12B of tube 12. The extendable flap 19 may be comprised of silicone or other suitable, medical grade material(s).

The extendable flap 19 preferably has a length (as measured from the position where it connects to outer wall 12B of tube 12 to the outermost edge 19D) that is at least 20%, or at least 30%, or at least 40%, or at least 50%, or at least 60%, or at least 70%, or at least 80%, or at least 90%, or at least 100%, or at least 120%, or at least 150%, or any amount from 20% to 150% of the outer circumference of the tube 12, as measured around outer surface 12B. The extendable flap 19 preferably has a thickness that is at least 10%, at least 20%, at least 30%, at least 40%, at least 50%, at least 60%, at least 70%, at least 80%, at least 90%, at least 100%, at least 110%, at least 120%, at least 130%, at least 1540%, at least 150%, or any amount from 10% to 150% of the thickness of the tube wall, as measured from outer surface 12B to inner surface 12A.

Figure 1D:
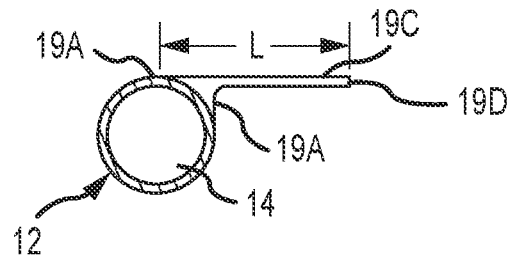
FIG. 1D is a cross-sectional view of the urinary catheter of FIG. 1C taken through line D-D.
Figure 1E:
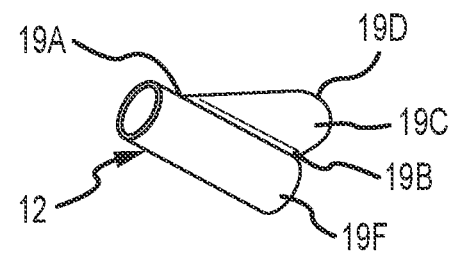
FIG. 1E is a partial side view of the urinary catheter of FIGS. 1C and 1D.

The extendable flap 19 may be of suitable thickness, length, and hardness suitable for use of the catheter. For example, the flap could utilize a 70A shore hardness with a 0.6 mm wall thickness as measured along length L from one edge of the flap 19 to the other as shown in FIG. 1D. Flap 19 has an axial length as measured from 19A to 19B that is preferably about equal to the length, or any amount from about 50% of the length to about 200% of the length, such as at least 10%, at least 20%, at least 30%, at least 40%, at least 50%, at least 60%, at least 70%, at least 80%, at least 90%, at least 100%, at least 110%, at least 120%, at least 130%, at least 140%, at least 150% at least 160%, at least 170%, at least 180%, at least 190%, or at least 200%.

The extendable flap 19 may comprise a thicker portion, or thicker ridge along each edge 19A as compared to the thickness of the rest of dual extendable flap 19. For example, the thickness at that location could be thicker than the thickness measured at the center of portion 190C by any amount from 10% to 100%, such as 10%, 20%, 30%, 40%, 50%, 60%, 70%, 80%, 90%, or 100%. This added thickness at that location may aid the user in collapsing the dual extendable flap 19 for insertion and also provide additional rigidity to support proper anchoring.

Extendable flap 19 can be integrally formed with the tube 12 or formed separately and attached to tube 12. As shown in this embodiment, extendable flap 19 is a separate component that is pulled over tube 12, and it has a body portion 19F.

Dual Extendable Flan

Figure 1F:
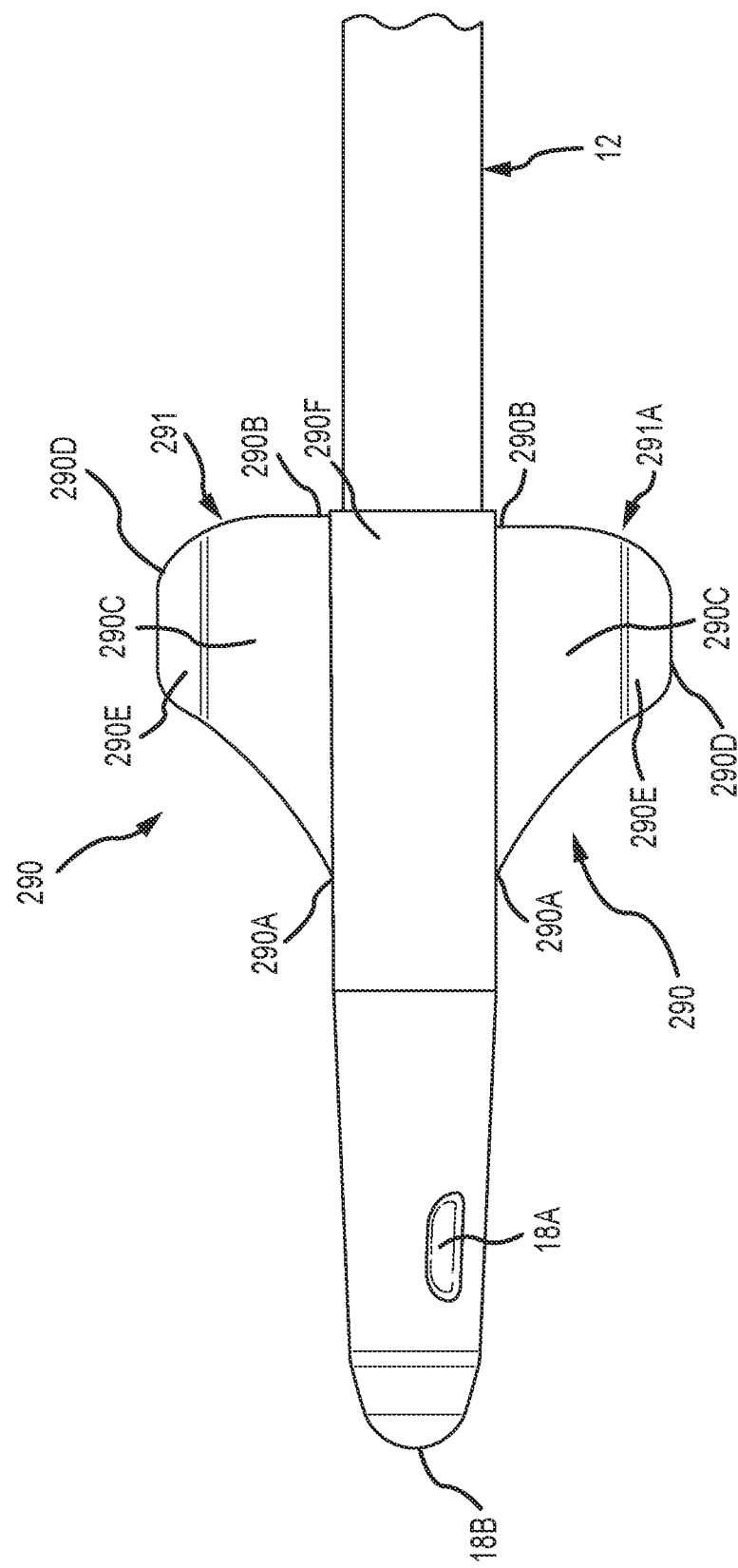
FIG. 1F is a top view of a urinary catheter with a dual extendable flap in its extended position.

The urinary catheter may comprise a dual extendable flap 290 on the distal end 18, as shown in FIGS. 1F-II and 2A. The dual extendable flap 290 as shown has two, identical flaps 290, 291 positioned 180 degrees from one another on tube 12. Flaps 291, 291A may, however, be positioned at any suitable location and need not be sized or shaped the same. The dual extendable flap 290 may be comprised of silicone or other suitable, medical grade material(s).

Figure 1G:
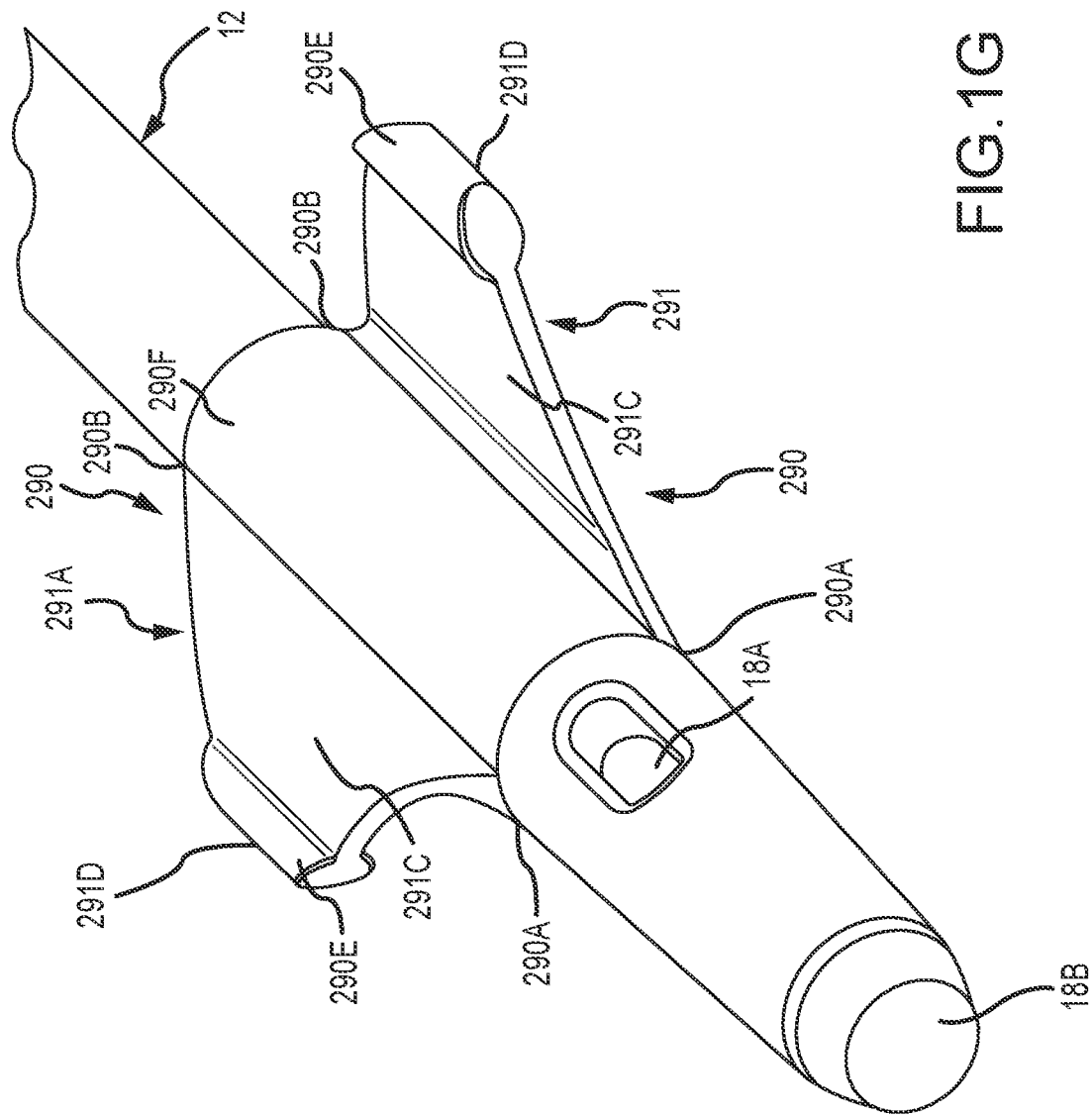
FIG. 1G is a rear, partial, perspective view of the urinary catheter of FIG. 1F.

Each flap 291, 291A has a first, contracted position in which it is positioned against the outer surface 12B of tube 12, and a second, extended position (shown in FIGS. 1F to 1H) in which flaps 291, 291A extend outward from the outer surface 12B of tube 12.

Each flap 291, 291A of the dual extendable flap 290 preferably has a length (as measured from the position at which it connects to outer wall 12B of tube 12 to the outermost edge 290D) that is at least 20%, or at least 30%, or at least 40%, or at least 50%, or at least 60%, or at least 70%, or at least 80%, or at least 90%, or at least 100%, or at least 120%, or at least 150%, or any amount from 20% to 150% of the outer circumference of the tube 12, as measured around outer surface 12B. Each flap 291, 291A preferably has a thickness at portion 290C that is at least 10%, at least 20⁰%, at least 30%, at least 40%, at least 50%, at least 60%, at least 70%, at least 80%, at least 90%, at least 100%, at least 110%, at least 120%, at least 130%, at least 1540%, at least 150%, or any amount from 10% to 150% of the thickness of the tube wall, as measured from outer surface 12B to inner surface 12A.

Each flap 291, 291A may be of suitable thickness, length, and hardness suitable for use of the catheter 10. For example, the dual extendable flap 290 could utilize a 70A shore hardness with a 0.6 mm wall thickness as measured along length L in section 190C. Each flap 291, 291A has an axial length as measured from 290A to 290B that is preferably about equal to the length, or any amount from about 50% of the length to about 200% of the length, such as at least 10%, at least 20%, at least 30%, at least 40%, at least 50%, at least 60%, at least 70%, at least 80%, at least 90%, at least 100%, at least 110%, at least 120%, at least 130%, at least 1540%, at least 150%, at least 160%, at least 170%, at least 180%, at least 190%, or at least 200%.

The dual extendable flap 290 may comprise a thicker portion, or thicker ridge along each edge 290A as compared to the thickness of the rest of dual extendable flap 190. For example, the thickness at that location could be ticker than the thickness measured at the center of portion 1900 by any amount from 10% to 100%, such as 10%, 20%, 30%, 40%, 50%, 60%, 70%, 80%, 90%, or 100%. This added thickness at that location may aid the user in collapsing the dual extendable flap 290 for insertion and also provide additional rigidity to support proper anchoring.

Further, each extendable flap 291, 291A as should has a bulb 290E at its tip. The bulb 290E as shown is circular in cross section and has a diameter that is greater than the thickness of section 290C. For example, each bulb 290E could have a diameter that is any amount from 10% to 200% greater than the thickness of section 290C, such as being greater by at least: 10%, 20%, 30%, 40%, 50%, 60%, 70%, 80%, 90%, 100%, 100%, 120%, 130%, 140%, 150%, 160%, 170%, 180%, 190%, or 200%.

Dual extendable flap 290 can be integrally formed with the tube 12 or formed separately and attached to tube 12. As shown in this embodiment, dual extendable flap 290 is a separate component that is pulled over tube 12, and it has a body portion 290F.

Valve

The valve 100 is preferably configured to restrict, or allow, fluid flow from the bladder 2000 (or other body part) out of the proximal end 16 of catheter 10. In the embodiment shown, the valve 100 is located in lumen 14 between the proximal end 16 and the retainer portion 20, although the valve 100 can be positioned at any suitable location in the lumen 14, or at the distal end 18 or proximal end 16 of catheter 10, as long as the valve can open to allow, and close to prevent fluid flow out of proximal end 16. As shown in this embodiment, the valve 100 is a magnetic valve, and wireless controller 6000 (described below) can be placed on or near valve 100 from outside of the patient's body to operate valve 100.

Figure 4A:
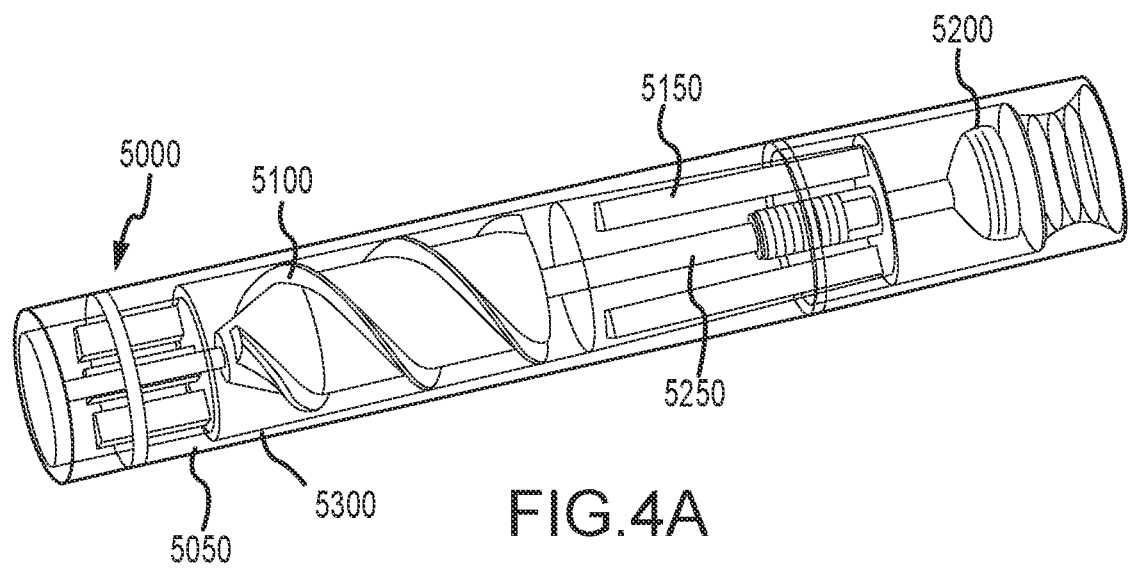
FIG. 4A is a close-up, open view of the proximal end of the urinary catheter of FIG. 1 showing a valve.
Figure 4B:
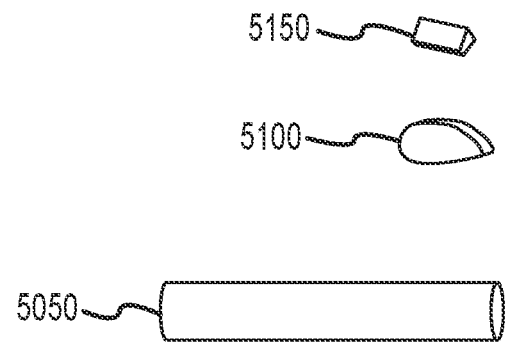
FIGS. 4B-4C show components of the valve of FIG. 4A.
Figure 4C:
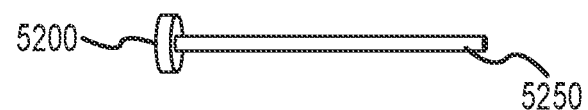
Figure 5:
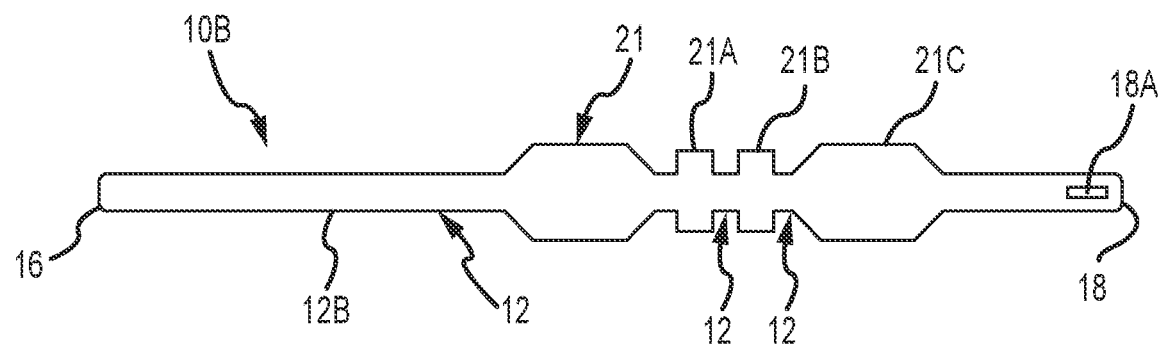
FIG. 5 is an exemplary embodiment of a urinary catheter according to aspects of the invention that has a plurality of retainer portions.
Figure 6:
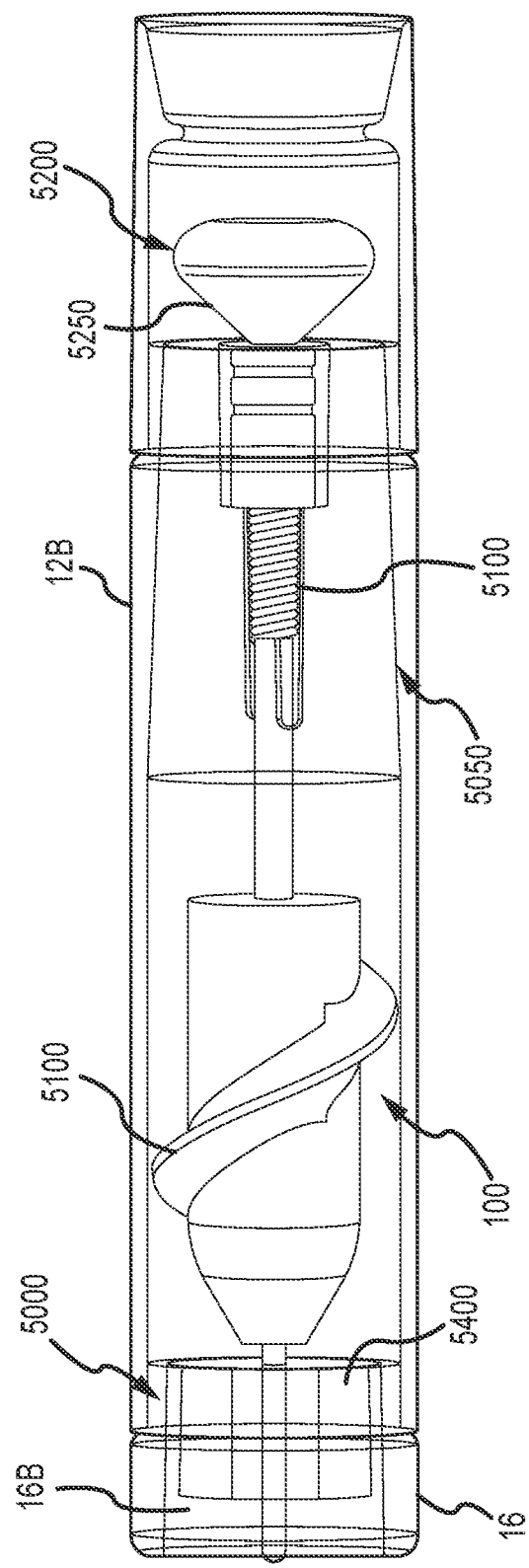
FIG. 6 is a side view of an alternative valve according to this disclosure.

The valve 100 preferably comprises a cylindrical body. As shown in FIGS. 4A and 6, the valve 100 includes a housing 5050, a screw portion 5100, a valve magnet 5150, a valve tip 5200, a spindle 5250, and an alignment tube 5300. The housing 5050 can comprise a cylindrical body. The screw portion 5100 can comprise a threaded body. The valve tip 5200 can be connected to the spindle 5250. The valve tip 5200 can be configured to open and close the valve. For example, the valve tip 5200 can comprise a conical surface corresponding to a seating structure of the valve opening 5400.

The screw portion 5100 can be movable inside the housing 5050. The housing 5050 and the screw portion 5100 can be in a threaded connection. The magnet can be connected to the screw portion 5100 and the spindle 5250. By moving the magnet 5150, the valve 100 can open and close. For example, the magnet 5150 can be moved by using an wireless controller 6000 (described below), shown in FIG. 7, to open and close the valve 100, such as by spinning magnet 5150, in order to activate the valve 100 and facilitate and/or control fluid flow. The valve 100 and the wireless controller 6000 can be configured to allow the user to increase or decrease the flow rate of the urine from the bladder 2500 by the wireless controller 6000 signaling the valve 100.

If valve 100 is a magnetic valve, as shown in this embodiment, when it is operated it pumps fluid, rather than simply allowing fluid to flow as a result of fluid pressure in the bladder 2500 or other body structure in which distal end 18 is positioned. Using the bladder 2500 as an example, by pumping fluid the bladder is more completely emptied, which can lead to relieving the bladder fewer times over a given period of time. Alternatively, the valve could be any structure that can be operated to (a) prevent the passage of fluid out of proximal end 16, and (b) allow fluid to flow past proximal end 16.

Catheter Mating Device

A system according to the invention can comprise a catheter 10 and a catheter mating device 1000, wherein the catheter mating device 1000 and catheter 10 are each configured to connect to one another so that catheter 10 can be moved by moving the catheter mating device 1000. As shown in FIGS. 8-14, the catheter mating device 1000 can be used to place the catheter 10 into a patient's body, and to remove the catheter 10 from the patient's body. The catheter mating device 1000 comprises a stem 1150 that includes: (a) a tube 1152 having an outer surface (or external wall) 1154 and a lumen 1162, (b) an inner cylinder 1160 having a distal end 1164 and a proximal end 1160E connected to a control 1520, and (c) a distal end 1170 with apparatus 1172.

The apparatus 1172 is a structure that operates mechanically to connect the stem to the proximal end of the catheter, thus connecting the catheter mating device 100 to catheter 10. Apparatus 1172 has a first, retracted position, wherein it can fit inside of the proximal end 16 of tube 12, and a second, expanded position, wherein it engages proximal end 16 and connects catheter mating device 100 to catheter 10.

Figure 8:
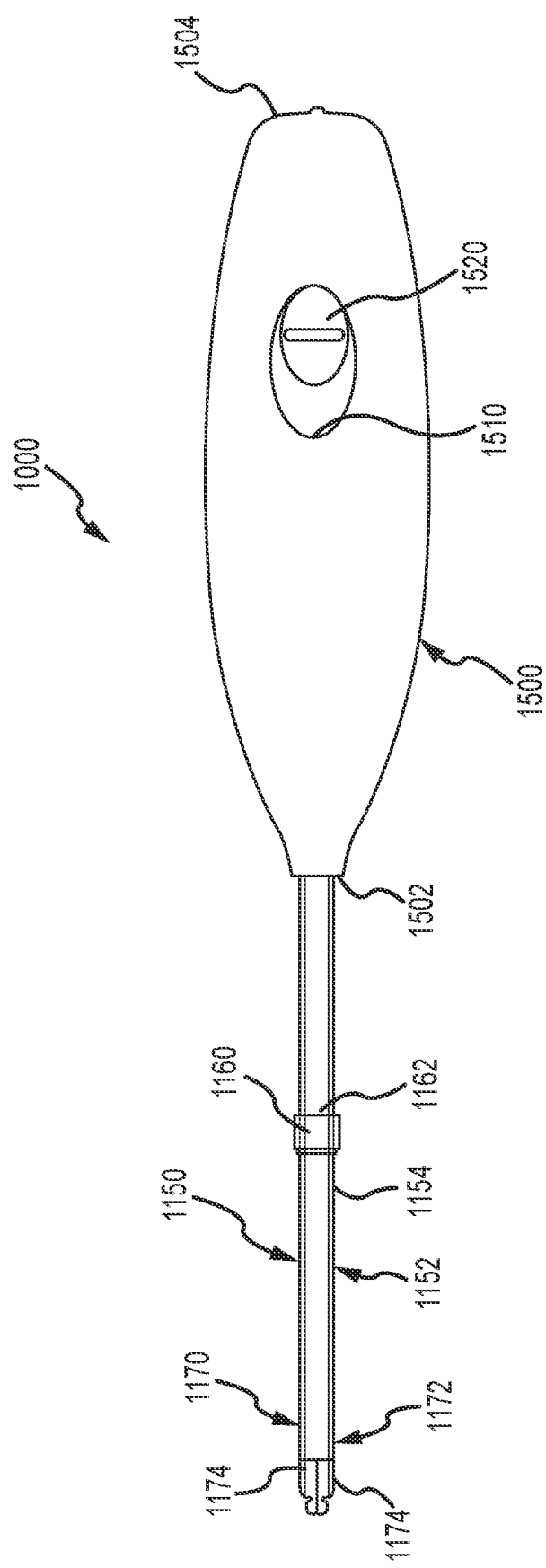
FIG. 8 is a top view of a catheter mating device according to this disclosure.
Figure 10A:
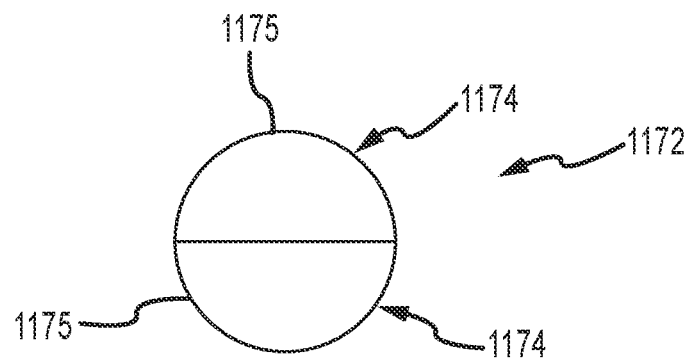
FIGS. 10A and 10B are end views of the distal end of the stem of the catheter mating device of FIG. 8.
Figure 10B:
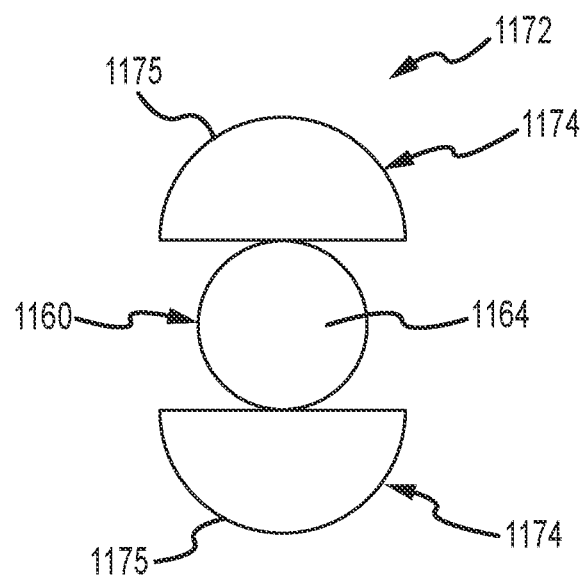
Figure 10C:
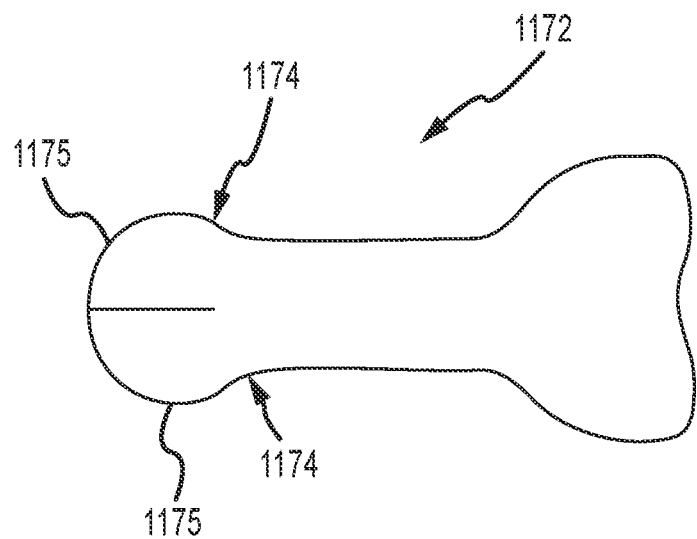
FIGS. 10C and 10D are partial, side views of the distal end of the stem of the catheter mating device of FIG. 8.

In this embodiment, the apparatus 1172 comprises tips 1174 that are configured to be positioned inside proximal end 16 (such as inside of engagement chamber 16B) when tips 1174 are in their first, retracted position and have a first distance between them (which may be zero distance because tips 1174 may touch when in the first, retracted position) as seen in FIGS. 8, 10A, and 10C. Tips 1174 can be moved to their second, expanded position in which they have a second distance between them that is larger than the first distance. In the second, expanded position, tips 1174 engage the inner wall of engagement chamber 16B, which connects catheter 10 to catheter mating device 1000. Once engaged, the catheter 10 can be moved through the urethra 2600 by using the catheter mating device 1000 either to push and advance, or pull and retract, the catheter 10.

When in their second, expanded position, the tips 1174 (as measured when they are not restricted by a structure, such as the inner wall of mating chamber 16B or another structure), can have a maximum outer distance across them that is the same, or greater than, the diameter of mating chamber 16B (or other inner portion of catheter 10, such as lumen 14, because mating chamber 16B need not be used) in order for tips 1174 to create an interference fit against the inner wall of mating chamber 16B (or other structure). The tips 1174 can be comprised of any suitable material, such as a plastic, metal, or a thermoplastic elastomer.

In some embodiments, the tips 1174 at distal end 1170 form a tapered configuration such that they facilitate proper alignment of the tips 1774 and engagement chamber 16B so that tips 1774 can be received inside of chamber 16B (or other structure of catheter 10, such as lumen 14). Tips 1174 may have rounded end portions 1175 that assist in engaging proximal end 16.

Figure 10D:
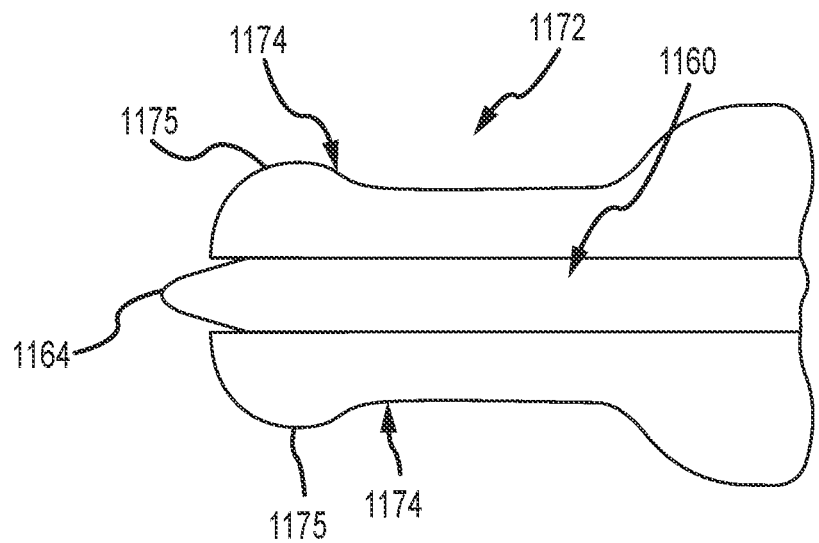

The catheter mating device 1000 in this embodiment comprises a cylinder 1160 positioned inside of outer tube 1152. The cylinder 1160 is operated to move from a retracted position to an extended position. When cylinder 1160 is in its extended position (as shown in FIGS. 10, 10B, and 10D), the cylinder 1160 moves between the tips 1174 and pushes them open to their second, extended position. When cylinder 1160 is in its retracted position (as shown in FIGS. 8, 10A, 10C, and 11-14) tips 1174 are in their first, retracted position.

The cylinder 1160 may be comprised of any suitable material, such as ABS or PTFE, and preferably has a tapered distal end 1164.

A user may operate the catheter mating device 1000 by moving the control 1520 to its second position, which move the apparatus 1172 to its second, expanded position, and by moving the control 1520 to its first position, in which the apparatus 1172 either moves to, or is moved to its first, retracted position. In the embodiment shown, control 1520 is a slide switch directly or indirectly connected to cylinder 1160. When control 1520 is in its first position, the cylinder 1160 is in its first, retracted position. When control 1520 is moved to its second position, cylinder 1160 is moved to its second, extended position, wherein it moves between tips 1174 and pushes them open to their second, expanded position.

Although tips 1174 are shown as the apparatus 1172, other strictures that can be mechanically expanded (as opposed to expanding utilizing gas or liquids) may be used. For example, there may more than two tips that are expanded in the manner described herein. Or, the tips or other structures may be expanded in any suitable manner. Alternatively, the tube 1152 of the stem 1150 could function as an outer sheath, and the apparatus could be attached to the cylinder 1160. In that example, the apparatus could be a metal mesh tube. Such an apparatus would be in its first, retracted position when contained inside of the tube 1152. The tube would be connected to the control 1520 and pulled back to expose the apparatus when the control 1520 is moved proximally (i.e., away from the catheter 10). That would permit the metal-mesh tube to automatically expand to its second, expanded position to engage proximal end 16. Or, utilizing the same structure, the cylinder 1160 including the apparatus could be connected to the control. In that case, a user could advance the cylinder 1160 and metal mesh tube out of the tube 1152, and the metal mesh tube would automatically expand to its second, expanded position. Alternatively, the stem could comprise an apparatus that is a flexible tube (comprised of rubber or flexible plastic) with one end of the tube connected to a first sleeve and another end connected to a second sleeve. The first sleeve and second sleeve would be coaxial and at least one could move relative the other. A user could then manipulate one or both of the sleeves to compress the tube causing it to bulge, i.e., expand in the center, and engage the inner wall of the proximal end 16 (which could be engagement chamber 16B) of catheter 10.

The stem 1150 in this embodiment has a length configured to enable a user to place catheter 10 in the urinary tract using the catheter mating device 1000. For example, in this embodiment stem 1150 may have a lengths (a) greater than the length of the penile urethra of a patient. (b) less than or equal to the length as measured from the membranous portion to the urethral orifice of a patient, and/or (c) less than the length of the penile urethra of a patient. In some embodiments, the stem 1150 is about 10 cm to 26 cm in length. Stem 1150 can include a fluid opening 1162 that is configured to allow fluid flow from the catheter 10 to pass through the lumen 1164 of stem 1150 and out of the proximal end 1152A of tube 1152, where the fluid can be collected or disposed, or pass through housing 1500 to be collected or disposed.

The tips of the tool and the cylinder may be designed in a configuration such that the maximum outer dimension of the tips in the expanded configuration is smaller than the stem. This may aid in preventing any unnecessary tissue damage to the penile urethra in the event that the user inserts or remove the tool with the tips in the expanded configuration without the catheter attached.

The catheter mating device 1000 may comprise an alternate stem 1150' that includes: (a) a tube 1152' having an outer surface (or external wall) 1154' and a lumen 1162, (b) an inner cylinder 1160 having a distal end 1164 and a proximal end 1160B connected to a control 1520, and (c) a distal end 1170' with apparatus 1172'. All components of stem 1150' are the same as for stem 1150 except as noted here. In all other respects, the structure and function of a catheter mating device 1000 is the same as previously described.

Turning now to FIGS. 11-14, an alternate distal stem 1150' of a catheter mating device 1000 is shown. Stem 1150' comprises an apparatus 1170' with tips 1174' that have a conical shape with a rounded end 1175' and lip, or ledge, 1177'. This configuration better assists tips 1174' in retaining end 16 of tube 12. Tips 1174' are configured to be positioned inside proximal end 16 (such as inside of engagement chamber 16B) when tips 1174' are in their first, retracted position. In that position tips 1174' have a first distance between them (which may be zero distance because tips 1174' may touch when in the first, retracted position) as best seen in FIGS. 11-14. Tips 1174' can be moved to their second, expanded position (not shown) in which they have a second distance between them that is larger than the first distance, as with tips 1174. In the second, expanded position, tips 1174' engage the inner wall of engagement chamber 16B, which connects catheter 10 to catheter mating device 1000. Once engaged, the catheter 10 can be moved through the urethra 2600 by using the catheter mating device 1000 either to push and advance, or pull and retract, the catheter 10.

Each tip 1174' has a outwardly curved section 1172', a recess 1171', a wall 1203', and a projection 1201'. Wall 1152' or stem 1150' includes openings 1152A'. Each wall 1203' is pressed into channel 1160 of stem 1150' until projection 1201' reaches an opening 1152' and extends therethrough. This mechanically retains a tip 1174' in position.

When in their second, expanded position, the tips 1174' (as measured when they are not restricted by a structure, such as the inner wall of mating chamber 16B or another structure), can have a maximum outer distance across them that is the same, or greater than, the diameter of mating chamber 16B (or other inner portion of catheter 10, such as lumen 14, because mating chamber 16B need not be used) in order for tips 1174' to create an interference fit against the inner wall of mating chamber 16B (or other structure). The tips 1174' can be comprised of any suitable material, such as a plastic, metal, or a thermoplastic elastomer.

In some embodiments, the tips 1174' at distal end 1170' form a tapered configuration such that they facilitate proper alignment of the tips 1774' and engagement chamber 16B so that tips 1174' can be received inside of chamber 16B (or other structure of catheter 10, such as lumen 14).

Housing

The catheter retainer portion 1000 can have a handle (or housing) 1500 at its proximal end. Housing 1500 may house a portion of the stem 1150 and/or cylinder 1160, and includes a control 1520. The housing 1500 is comprised of any suitable material such as PVC or other plastic. Housing 1500 has body portion 1500A, which can be formed of two connected portions 1550 and 1580 as shown in FIG. 9. Body portion 1500A has a distal end 1502, a proximal end 1504, and a cavity 1506. An opening 1510, which communicates with cavity 1506, is in surface 1588. A control 1520 is positioned in cavity 1506 and extends through opening 1510 where it can be accessed by a user.

As shown, control 1520 is a slide switch that can be moved from a first (proximal) position to a second (distal position). Control 1520 has a ridge 1522 that can be pushed by a user's finger, a body portion 1524 that extends through opening 1510, and a base 1526 positioned in cavity 1506. Fasteners 1528 extend through apertures 1530 to retain control in housing 1500.

In the embodiment shown, cylinder 1160 is connected to control 1520. A user can move switch 1520 in a distal direction to push cylinder 1160 to its extended position, wherein the cylinder 1160 moves the apparatus to its second, expanded position. A user can move switch 1520 in a proximal direction, wherein the cylinder 1160 moves to its retracted position away from the apparatus 1172 and the apparatus moves to its first, retracted position. Although a manual slide switch is described herein, control 1520 could be any structure that can operate to directly or indirectly move the apparatus to its second, expanded position.

The proximal end 1152A of tube 1152 is retained inside of cavity 1506. If fluid enters lumen (or passageway) 1162 it exits the proximal end 1152A, and can flow through housing 1500, where it exits opening 1504A at proximal end 1504. This allows for relatively easy collection or disposal of fluid from the body in which catheter 10 is positioned. In one embodiment, the stem 1150 has a length of about 10 cm to 26 cm.

Materials

The catheter 10 and the stem 1170 of catheter mating device 1000 are, respectively, constructed in a shape and of a material that is conducive for their intended use. For example, the catheter 10 and stem 1170 may be constructed of any material or materials suitable for catheters used in the body (such as PVC, latex, silicone, polyurethane or any suitable blend of these materials).

Packazine and Use

The catheter mating device 1000 and the catheter 10 can be carried in a sterilized pouch. A user may open the pouch comprising a catheter 10 and the catheter mating device 1000 and insert the catheter 10 into the lower urinary tract, and could use catheter mating device 1000 before inserting the catheter 10 into orifice 2700 of urethra 2600. Such packaging may also be designed to be durable and withstand transportation in a home-use setting. This period of time may last anywhere between 2-180 days.

Wireless Controller

Figure 7:
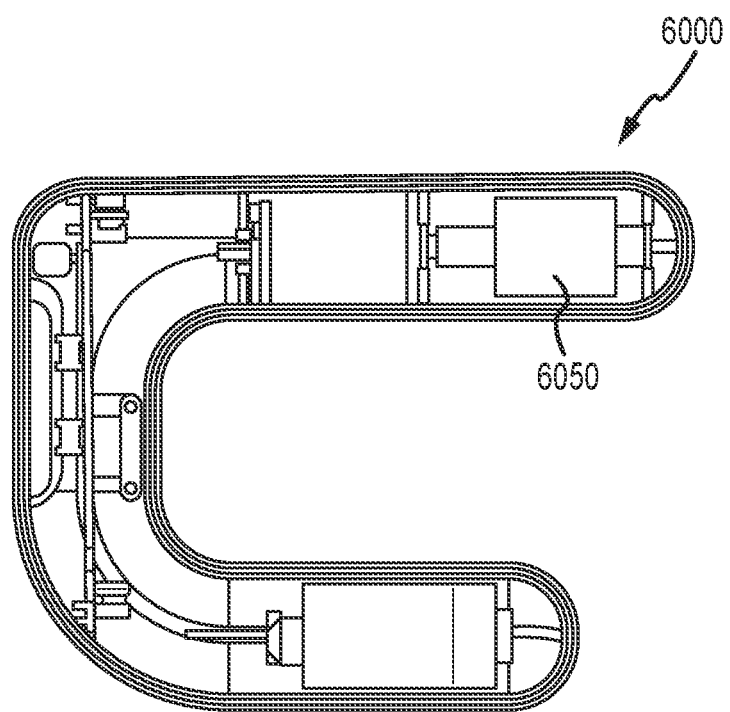
FIG. 7 is a side, cross-sectional view of a valve controller.

Urine in the bladder (or fluid from another area in the body) can be voided when the user utilizes an external wireless controller 6000 (shown in FIGS. 2, 3 and 7) to operate the valve 100 and allow urine to travel through the lumen 14, past proximal end 16, and out of catheter 10. As shown in FIG. 7, the wireless controller 6000 can comprise an wireless controller magnet 6050, a power source 6100, an electronic circuitry 6150, and one or more inputs 6200, 6250. In some embodiments, the one or more inputs 6200, 6250 can comprise a first input to open the valve 100 and a second input to close the valve 100. The wireless controller comprises two or more input modes, such as a close mode, an open mode, and an off mode. The valve 100 is closed (or off) when the wireless controller 6000 is in its close mode, and is open (or in operation) when the wireless controller is in its open mode. The valve 100 can remain closed or remain opened when the wireless controller 6000 is in its off mode. In some embodiments, the circuitry 6150 can comprise software configured to automate the process of controlling fluid flow from bladder. A user can place the wireless controller 6000 near the valve 100, e.g., on the skin of the patient between the scrotum and the shaft of the penis. The user may press the input 6200 to operate the magnet 6050.

Sensors and Data Collection

The catheter 10 can include one or more sensors configured to transmit data from the patient's body. The data can comprise one or more of: fluid pressure of urine in the bladder and/or urethra, volume of fluid in the bladder, temperature of fluid in the bladder and/or urethra, acidity of fluid in the bladder and/or urethra, bacteria type and quantity of fluid in the bladder and/or urethra, chemical composition of fluid of fluid in the bladder and/or urethra, fluid flow during emptying of the bladder when valve 100 is open, or actuated. One or more sensors are of a type known to those skilled in the relevant art, although the claims are not limited to presently-known sensors. One or more sensors on or inside of catheter 10 would have basically consistent sensor location and extended sensors measurements within the body to better monitor patient conditions, without having sensors taken out of the body.

The one or more sensors can be placed at any suitable location on catheter 10. For example, one or more sensors can be placed on or near the distal tip 18 of catheter 10, in which case the one or more sensors would be positioned in the bladder if catheter 10 is configured for use in the lower urinary tract of a human male. A catheter 10 could comprise different inner diameters can include a diameter in which a sensor would fit, such that the sensor is retained within lumen 14 without preventing fluid flow through the lumen. For example, a sensor could be distal to openings 18A. The outer wall 12A of the tube 12 would then prevent the sensor from contacting body tissue or fluid. One or more sensors may be positioned on or in retainer portion 20.

In one embodiment, one or more sensors can determine the pressure of urine within the bladder and send a signal to a processor that sends the information to a computing device, or the one or more sensors could send data directly to the computing device. The computing device, which can be any device, such as a PC or other computer, cell phone, dedicated catheter device, the wireless controller, or the catheter mating device, can have software that determines whether and when fluid (such as urine) needs to be drained from the bladder. The computing device can notify the user in any manner to drain urine from his/her bladder. In some embodiments, the one or more sensors can be used to determine when urine has been sufficiently drained from the bladder, such as by determining that the pressure level within the bladder has dropped below a certain level. This information can be used to close the valve 100 and halt the flow of urine from leaving the bladder. In some embodiments, the one or more sensors can include acoustics to determine the volume of urine in the bladder. Different types of sensors can be placed in or on the catheter 10 to determine metrics related to the health of areas of the body, such as bladder health.

In some embodiments, a sensor can be configured to detect the flow rate of urine through the valve 100. For example, a catheter system 10 can comprise software configured to detect the flow rate of urine through the valve 100 by measuring the electric current draw of the valve motor by wireless controller 6000. The catheter system 10 can comprise an external computing device comprising a memory in wireless communication (either intermittently or continuously) with the electronic circuitry 6150 of wireless controller 6000 to record store and/or transmit data measured by one or more sensors.

In some embodiments, one or more sensors can function without a power source. By constructing the sensor in a specific manner the external unit can observe changes in the resonant frequency characteristics.

The data collected by the one or more sensors can be stored, analyzed, and/or transmitted via software resident on a device outside of the body in which the one or more sensors is positioned. The software may utilize machine-learning algorithms to predict and interpret the measurements.

The sensor can be configured to change its mechanical properties (e.g. size or shape) based on pressure changes inside the bladder. The user can use an external device to detect changes in mechanical properties of the sensor by, for example, sending and/or receiving magnetic or electronic signals.

Catheter 10 may also include a second lumen to house one or more antennas that communicate in any suitable manner with the one or more sensors and with one or more external devices, such as a transducer or external computer device. The antennas can send data from the one or more sensors to one or more external devices and signals from one or more external devices to any of the one or more sensors. The antennas can have a power source.

A programmable microcontroller ("PMC") may be included in catheter 10, or in catheter mating device 1000. The programmable microcontroller could communicate with all or any other electronic components of a system as disclosed herein. For example, the PMC could communicate with one or more of the sensors, antennae, and an outside computer or other controller to relay information, store information, or turn a sensor or antennae on or off. The PMC could be reprogrammed by an operator depending upon the function desired.

The PMC could comprise, or be physically or electrically connected to, a flexible circuit board would allow for some movement within a user's body. Components that could be physically or electrically connected to the circuit board include one or more of (a) a separate processor; (b) one or more sensors; (c) a radio transmission module (such as Bluetooth or WIFI); and (d) an antenna.

External Computer Device

The catheter system can comprise a computing device external to the patient's body. The external computing device may comprise a memory wirelessly connected to the electronic circuitry 6150 to receive operational parameters of the lower urinary tract. In some embodiments, the computing device can have a software which can be used to interpret data gathered by the one or more sensors. For example, the one or more sensors may be a pressure sensor and the computing device can analyze data pressure received from the sensor to be used to alert a user about when the user's bladder is likely to contract and void.

Some Non-Limiting Examples of this Disclosure

The following examples 1-145 are sometimes referred to herein as the First Set of Examples.

Example 1: A Catheter System Comprising:
(a) a catheter comprising (i) a tube, the tube having (A) a wall with an outer surface, the outer surface having a first cross-sectional area, (B) a lumen, (C) a distal end with one or more openings in communication with the lumen, and (D) a proximal end with an opening in communication with the lumen; (ii) a valve that is operated to be in (A) a closed configuration, wherein fluid does not flow out of the proximal end, or (B) an open configuration in which fluid does flow out of the proximal end; and (iii) a retainer portion between the distal end and the proximal end, the retainer portion having (A) an outer wall that has an outer surface, an inner surface, and a maximum cross-sectional area at least twice as great as the first cross-sectional area, (B) a cavity inside of the outer wall, (C) a core inside of the cavity, the core having a passage in which the tube is positioned, and (D) at least one expansion structure positioned inside of the cavity, the at least one structure being configured to contact an inner surface of the outer wall and exert outward force thereon; and (b) a catheter mating device comprising: a stem having a proximal end and a distal end; wherein the distal end includes an apparatus having (i) a first configuration with a first distal cross-sectional area, and (ii) a second configuration with a second distal cross-sectional area that is greater than the first distal cross-sectional area; the apparatus being configured to be received in the proximal end of the catheter when in its first configuration, and configured to engage the proximal end of the catheter when in its second configuration.

Example 2: The catheter system of example 1, wherein the retainer portion has a maximum cross-sectional area that is 3-5 times greater than the first cross-sectional area.

Example 3: The catheter of example 1, wherein the retainer portion has a maximum cross-sectional area that is 1.5-3 times larger than the first cross-sectional area.

Example 4: The catheter system of any of examples 1-3, wherein the retainer portion has a length and the maximum cross-sectional area is at a center of the length.

Example 5: The catheter system of any of examples 1-4, wherein the retainer portion has a length and the maximum cross-sectional area is along part of the length.

Example 6: The catheter system of any of examples 1-3, wherein the retainer portion has a top surface and the maximum cross-sectional length along the entire top surface.

Example 7: The catheter system of any of examples 1-6, wherein the length of the retainer portion is between 1 cm and 10 cm.

Example 8: The catheter system of any of examples 1-7, wherein the maximum cross-sectional area is between $(4 \text{ mm})^2\pi$ and $(25 \text{ mm})^2\pi$.

Example 9: The catheter system of any of examples 1-7, wherein the retainer portion has a circular cross-section at its maximum cross-sectional area, and a diameter of between 5 mm and 10 mm at the maximum cross-sectional area.

Example 10: The catheter system of any of examples 1-9, wherein the retainer portion has a hardness of between 1 and 70 Shore A.

Example 11: The catheter system of any of examples 1-10, wherein the wall of the catheter has a hardness of between 30 Shore A and 55 Shore D.

Example 12: The catheter system of any of examples 1-11, wherein the retainer portion is comprised of silicone.

Example 13: The catheter system of any of examples 1-12, wherein the retainer portion is positioned between the valve and the distal end.

Example 14: The catheter system of any of examples 1-12, wherein the retainer portion comprises one or more of grooves and mounds.

Example 15: The catheter system of any of examples 1-14 that is configured to be completely retained inside of a urinary tract of a male human.

Example 16: The catheter system of any of examples 1-15, wherein the retainer portion extends outward from the outer surface of the wall.

Example 17: The catheter system of any of examples 1-16, wherein the retainer portion is configured to be compressed to have a maximum cross-sectional area of 0.3 mm to 8.0 mm when moved through a penile urethra.

Example 18: The catheter system of any of examples 1-17, wherein at least part of the retainer portion is configured to be positioned within the bulbar urethra of the patient when the catheter is positioned inside a urinary tract of a human male.

Example 19: The catheter system of any of examples 1-18, wherein the retainer portion is positioned on the tube.

Example 20: The catheter system of example 19, wherein the retainer portion includes a passage therethrough and part of the tube is positioned in the passage.

Example 21: The catheter system of example 1, wherein the retainer portion has (a) a distal section that has (a) a smaller cross-sectional area than the maximum cross-sectional area, and (b) a proximal section that has a smaller cross-sectional area than the maximum cross-sectional area.

Example 22: The catheter system of any of examples 1-21, wherein the valve is a magnetic valve.

Example 23: The catheter system of any of examples 1-22, wherein the valve is positioned in the lumen.

Example 24: The catheter system of any of examples 1-23 that further includes an engagement chamber at the proximal end, wherein the engagement chamber is about 10 Shore A to 55 Shore D harder than the wall.

Example 25: The catheter system of any of examples 1-23 that further includes an engagement chamber that has a diameter that is the same as a diameter of the lumen.

Example 26: The catheter system of any of examples 1-25 that further includes one or more sensors on or in the catheter.

Example 27: The catheter system of example 26 comprising a sensor housing, wherein the one or more sensors are positioned inside of the sensor housing.

Example 28: The catheter system of example 26 wherein the one or more sensors are positioned inside of the lumen.

Example 29: The catheter system of example 26, wherein the one or more sensors are positioned in a bladder when the catheter is positioned in a lower urinary tract of a human male.

Example 30: The catheter system of example 26, wherein the catheter comprises a distal tip and at least a portion of the one or more sensors is positioned inside of the distal tip.

Example 31: The catheter system of example 26, wherein the one or more sensors are positioned at least partially in the lumen.

Example 32: The catheter system of any of examples 26-31 that has one sensor.

Example 33: The catheter system of any of examples 26-31 that has a plurality of sensors.

Example 34: The catheter system of any of examples 26-33, wherein the one or more sensors are configured to collect data of the patient, the data comprising one or more of fluid pressure inside of the bladder, fluid volume inside of the bladder, temperature inside of the bladder, acidity of urine, bacteria level and type in urine, chemical composition of urine, motion of the patient, location of the patient, and fluid flow when emptying the bladder.

Example 35: The catheter system of any of examples 1-34, wherein the catheter mating device further includes a housing connected to the proximal end of the stem.

Example 36: The catheter system of example 35, wherein the proximal end of the stem is positioned inside of the housing.

Example 37: The catheter of any of examples 1-36, wherein the stem has an internal passageway configured to the transport bodily fluid.

Example 38: The catheter system of example 37, wherein the internal passageway is inside of an external wall.

Example 39: The catheter system of example 38, wherein the external wall is transparent or translucent.

Example 40: The catheter system of example 37, wherein the internal passageway is coaxial with the external wall.

Example 41: The catheter system of example 35, wherein the housing includes a control having a first position and a second position, and the distal end of the stem is in its first position when the control is in its first position, and the distal end of the stem is in its second position when the control is in its second position.

Example 42: The catheter system of example 41, wherein the control is a slide button on an outside surface of the housing, the slide button moveable between the first position of the control and the second position of the control.

Example 43: The catheter system of example 42, wherein the slide button is connected to the cylinder.

Example 44: The catheter system of any of examples 35, 36 or 41-43, wherein the housing includes a cavity, a housing proximal end and a housing distal end, and the housing proximal end is open to the cavity, and the housing proximal end has an opening through which fluid can pass.

Example 45: The catheter system of any of examples 35, 36 or 41-44, wherein the housing is comprised of plastic.

Example 46: The catheter system of any of examples 35, 36 or 41-45, wherein the housing includes an opening in one side, wherein the opening communicates with the cavity and the control is positioned in the opening.

Example 47: The catheter system of any of examples 1-46, wherein the tube has a durometer of between 35 Shore A and 90 Shore D.

Example 48: The catheter system of any of examples 1-47, wherein the apparatus comprises a plurality of tips moveable from the first position to the second position.

Example 49: The catheter system of example 48, wherein the apparatus comprises two tips.

Example 50: The catheter system of example 49, wherein the tips move apart and into the second position when the control is moved to its second position.

Example 51: The catheter system of example 48 that further includes a cylinder attached to the control, and the cylinder is movable between a between a retracted position and an extended position, wherein the cylinder in its extended position contacts the tips and moves apart and into the second position, when the control is in its second position.

Example 52: The catheter system of example 51, wherein the cylinder in its retracted position does not contact the tips and the tips arc in their first position, when the control is in its first position.

Example 53: The catheter system of any of examples 51-52, wherein the cylinder has a durometer of between 60 Shore A and 90 Shore D.

Example 54: The catheter system of any of examples 1-53, wherein the distal end of the stem has a tip of a durometer of 5-65 Shore A greater than the durometer of an outer tube of the stem.

Example 55: The catheter system of any of examples 1-54 that further includes an wireless controller that activates the valve.

Example 56: The catheter system of any of examples 26-34, further comprising an external computing device configured to process and store patient data, wherein the sensors are configured to wirelessly transmit data to the external computing device.

Example 57: The catheter system of example 56, wherein the external computing device is wirelessly connected to the valve and the valve is configured to actuate based on a command by the external computing device.

Example 58: The catheter system of any of examples 26-34 that further includes one or more antennas, wherein the antennas are configured to transmit data received from the one or more sensors.

Example 59: The catheter system of any of examples 26-34, wherein the catheter includes a second lumen and the one or more antennas are positioned in the second lumen.

Example 60: The catheter system of example 56 that further includes one or more antennas, wherein the antennas are configured to transmit data received from the one or more sensors to an external computing device.

Example 61: The catheter system of example 58, wherein the one or more antennas have a power source positioned in the catheter.

Example 62: The catheter system of any of examples 1-62, wherein the power source is a battery.

Example 63: The catheter system of example 1 that includes a plurality of retainer portions.

Example 64: The catheter system of example 63, wherein at least one of the plurality of retainer portions has a different size than the other of the plurality of retainer portions.

Example 65: The catheter system of example 63, wherein at least one of the plurality of retainer portions has a different shape than the other of the plurality of retainer portions Example 66: A catheter comprising:
(a) a tube, the tube having (i) a wall with an outer surface, the outer surface having a first cross-sectional area, (ii) a lumen, (iii) a distal end with one or more openings in communication with the lumen, and (iv) a proximal end with an opening in communication with the lumen,
(b) a valve that is operated to be in (i) a closed configuration, wherein fluid does not flow out of the proximal end, or (ii) an open configuration in which fluid does flow out of the proximal end; and
(c) a retainer portion between the distal end and the proximal end, the retainer portion having a maximum cross-sectional area at least 50% greater than the first cross-sectional area.

Example 67: The catheter of example 66 that has a length of 173 mm to 253 mm.

Example 68: The catheter of example 66 or 67, wherein the retainer portion is 48 mm to 105 mm from a closest of the one or more openings in the distal end of the catheter.

Example 69: The catheter of any of examples 66-68, wherein the proximal end has a proximal tip and the distance from the proximal tip to the closest of the one or more openings is 159 mm to 247 mm.

Example 70: The catheter of any of examples 66-69, wherein the retainer portion has a first end and a second end, and a first tapered portion at the first end and a second tapered portion at the second end.

Example 71: The catheter of example 70, wherein the first tapered portion extends from the outer diameter on the tube to the maximum diameter of the retainer portion, and the second tapered portion extends from the outer diameter on the tube to the maximum diameter of the retainer portion.

Example 72: The catheter of example 71, wherein the first tapered portion has a length of 4 mm to 8 mm, and the second tapered portion has a length of 10 mm to 25 mm.

Example 73: The catheter of any of examples 66-72 that further includes a second lumen that includes one or more of: one or more sensors, and one or more antennas.

Example 74: The catheter of any of examples 66-72 that further includes a second lumen that includes an antenna.

Example 75: The catheter of example 74, wherein the second lumen has a length and the antenna is at least half the length.

Example 76: The catheter of example 74, wherein the second lumen has a length and the antenna is extends at least 10°A. or 80%, or 90% of the length.

Example 77: The catheter of example 73, wherein the second lumen has a length equal to a length of the lumen.

Example 78: The catheter of any of examples 73-77, wherein the antenna is in electrical contact with one or more sensors positioned on or in the catheter.

Example 79: The catheter of example 78, wherein the antenna is physically connected to the one or more sensors.

Example 80: The catheter of any of examples 73-79 that has a plurality of sensors.

Example 81: The catheter of example 73, wherein the one or more sensors are positioned at one or more of: the distal end of the catheter, inside the lumen of the catheter, and in or on the retainer portion.

Example 82: The catheter of any of examples 66-81, wherein the retainer portion has an outer surface, and one or more of dimples, depressions, and ribs on the outer surface.

Example 83: The catheter of any of examples 66-82, wherein the proximal end has a proximal tip and a raised ridge at the proximal tip.

Example 84: The catheter of example 83, wherein the raised ridge has a diameter that is 0.5 to 1.0 mm greater that a diameter of the tube.

Example 85: The catheter of any of examples 66-84 that further includes a mating chamber at the proximal end, the mating chamber being harder than the tube.

Example 86: The catheter of example 85, wherein the mating chamber has a durometer of between 45-65 Shore D.

Example 87: The catheter of example 85, wherein the mating chamber has a durometer of between 55-90 Shore D Example 88: The catheter of example 85, wherein the mating chamber has a durometer of 55 Shore D.

Example 89: The catheter of any of examples 85-88, wherein the tube has a durometer of 50-65 Shore A.

Example 90: The catheter of any of examples 85-88, wherein the tube has a durometer of 60 Shore A.

Example 91: The catheter of any of examples 85-88, wherein the tube has a durometer of 10-30 Shore A.

Example 92: The catheter of any of examples 66-91, wherein the tube comprises silicone.

Example 93: The catheter of any of examples 73 or 78-81, wherein the one or more sensors are configured to collect data of the patient, the data comprising one or more of: fluid pressure inside of the bladder, fluid volume inside of the bladder, temperature inside of the bladder, acidity of urine, bacteria level and type in urine, chemical composition of urine, motion of the patient, location of the patient, and fluid flow when emptying the bladder.

Example 94: The catheter system of any of examples 1-65, wherein the catheter has a length of 173 mm to 223 mm.

Example 95: The catheter system of any of examples 1-65, wherein the retainer portion is 48 mm to 75 mm from a closest of the one or more openings in the distal end of the catheter.

Example 96: The catheter system of any of examples 1-65, wherein the proximal end has a proximal tip and the distance from the proximal tip to the closest of the one or more openings is 159 mm to 197 mm.

Example 97: The catheter system of any of examples 1-65, wherein the retainer portion has a first end and a second end, and a first tapered portion at the first end and a second tapered portion at the second end.

Example 98: The catheter system of example 97, wherein the first tapered portion extends from the outer diameter on the tube to the maximum diameter of the retainer portion, and the second tapered portion extends from the outer diameter on the tube to the maximum diameter of the retainer portion.

Example 99: The catheter system of example 97, wherein the first tapered portion has a length of 4 mm to 8 mm, and the second tapered portion has a length of 10 mm to 25 mm.

Example 100: The catheter system of any of examples 1-65, wherein the catheter further includes a second lumen that includes one or more of: one or more sensors, and one or more antennas.

Example 101: The catheter system of any of examples 1-65, wherein the catheter further includes a second lumen that includes one or more antennas.

Example 102: The catheter system of example 101, wherein the second lumen has a length and at least one antenna is at least half the length.

Example 103: The catheter system of example 101, wherein the second lumen has a length and the antenna is at least 70%, or 80%, or 90% of the length.

Example 104: The catheter system of example 73, wherein the second lumen has a length equal to a length of the lumen.

Example 105: The catheter system of any of examples 101-104, wherein the antenna is in electrical contact with one or more sensors positioned on or in the catheter.

Example 106: The catheter system of example 105, wherein the antenna is physically connected to the one or more sensors.

Example 107: The catheter system of any of examples 94-106 that has a plurality of sensors on or in the catheter.

Example 108: The catheter system of example 107, wherein the one or more sensors are positioned at one or more of: the distal end of the catheter, completely or totally inside a lumen of the catheter, and/or on or in the retainer portion.

Example 109: The catheter system of any of examples 1-65 or 94-108, wherein the retainer portion has an outer surface, and one or more of dimples, depressions, and ribs on the outer surface.

Example 110: The catheter system of any of examples 1-65 or 94-109, wherein the proximal end has a proximal tip and a raised ridge at the proximal tip.

Example 111: The catheter system of example 110, wherein the raised ridge has a diameter that is 0.5 to 1.0 mm greater that a diameter of the tube.

Example 112: The catheter system of any of examples 1-65 or 94-111 that further includes a mating chamber at the proximal end, the mating chamber being harder than the tube.

Example 113: The catheter system of example 112, wherein the mating chamber has a durometer of between 45-65 Shore D.

Example 114: The catheter system of example 112, wherein the mating chamber has a durometer of between 55-90 Shore D.

Example 115: The catheter system of example 112, wherein the mating chamber has a durometer of 55 Shore D.

Example 116: The catheter system of any of examples 1-65 or 94-115, wherein the tube has a durometer of 50-65 Shore A.

Example 117: The catheter system of any of examples 1-65 or 94-115, wherein the tube has a durometer of 60 Shore A.

Example 118: The catheter system of any of examples 1-65 or 94-115, wherein the tube has a durometer of 10-30 Shore A.

Example 119: The catheter system of any of examples 1-65 or 94-115, wherein the tube comprises silicone.

Example 120: The catheter system of any of examples 1-65 or 94-119, wherein the catheter further comprises one or more sensors configured to collect data of the patient, the data comprising one or more of: fluid pressure inside of the bladder, fluid volume inside of the bladder, temperature inside of the bladder, acidity of urine, bacteria level and type in urine, chemical composition of urine, motion of the patient, location of the patient, and fluid flow when emptying the bladder.

Example 121: The catheter system of any of examples 1-65 or 94-120, wherein the lumen has a diameter of any amount from 0.1 mm to 5.5 mm.

Example 122: The catheter system of any of examples 1-65 or 94-121, wherein the retainer portion has a length of any amount from about: 1 cm to 10 cm, or 2 cm to 8 cm, or 3 cm to 7 cm, or 4 cm to 6 cm.

Example 123: The catheter system of any of examples 1-65 or 94-122, wherein the retainer portion has a top surface that has a length of any amount from: 1 cm to 10 cm.

Example 124: The catheter system of any of examples 1-65 or 94-123, wherein the retainer portion has a top surface and the retainer portion has a length, and the length of the retainer portion is about 10%, or about 20%, or about 30%, or about 40%, or about 50%, or about 60%, or about 70%, or about 80%, or about 90%, or about 95%, of the length of the retainer portion.

Example 125: The catheter system of any of examples 1-65 or 94-124, wherein the maximum cross-sectional area of the retainer portion is any amount from: $(4 \text{ mm})^2 \pi$ to $(25 \text{ mm})^2 \pi$, or $(6 \text{ mm})^2 \pi$ to $(10 \text{ mm})^2 \pi$, or $(5 \text{ mm})^2 \pi$ to $(10 \text{ mm})^2 \pi$.

Example 126: The catheter system of any of examples 1-65 or 94-126, wherein the retainer portion at the maximum cross-sectional area can be compressed, by a force of an amount selected from the range of: 1 lb. to 10 lbs., or 2 lbs. to 20 lbs.; wherein the force is applied substantially equally to an outer surface of the retainer portion at the maximum cross-sectional area compresses to any percentage of its original cross-sectional area from: 20%-75%.

Example 127: A catheter mating device comprising: a stem having a proximal end and a distal end; and wherein the distal end includes an apparatus having a first configuration with a first cross-sectional area and a second configuration with a second cross-sectional area that is greater than the first cross-sectional area.

Example 128: The catheter mating device of example 127 that further includes a housing at the proximal end of the stem, the housing having a control moveable between a first position and a second position, wherein the apparatus is in its first, retracted position when the control is in its first position, and the apparatus is in its second, expanded position when the control is in its second position.

Example 129: The catheter mating device of example 128, wherein the control is connected to a cylinder that is part of the stem.

Example 130: The catheter mating device of example 128 or 129, wherein the housing comprises a distal end, a proximal end, a cavity, and an opening in the proximal end, wherein the opening communicates with the cavity.

Example 131: The catheter mating device of any of examples 127-130, wherein the apparatus comprises a plurality of tips moveable from the first, retracted position to the second, expanded position.

Example 132: The catheter mating device of example 131, wherein the apparatus comprises two tips.

Example 133: The catheter mating device of any of examples 127-132, wherein the apparatus comprises a plurality of tips, and the cylinder is movable between a between a retracted position and an extended position, wherein the cylinder in its extended position it contacts the tips and moves them apart and into the second, expanded position.

Example 134: The catheter mating device of example 133, wherein the cylinder has a retracted position in which it does not contact the tips and the tips are in their first position.

Example 135: The catheter mating device of any of examples 128-134, wherein the apparatus comprises a plurality of tips, and the tips move apart and into the second, expanded position when the control is moved to its second position.

Example 136: The catheter mating device of any of examples 128-135, wherein the control is a slide button on an outside surface of the housing, the slide button moveable between the first position of the control and the second position of the control.

Example 137: The catheter mating device of any of examples 128-136, wherein the housing has a first side and a second side, and the second side has a side opening in communication with the cavity, wherein the control is positioned partially in the cavity and extends through the side opening.

Example 138: The catheter mating device of any of examples 128-137, wherein the proximal end of the stem is positioned inside of the housing.

Example 139: The catheter mating device of any of examples 127-138, wherein the stem has an internal passageway configured to the transport bodily fluid therethrough.

Example 140: The catheter mating device of example 139, wherein the internal passageway is inside of an external wall.

Example 141: The catheter mating device of example 140, wherein the internal passageway is coaxial with the external wall.

Example 142: The catheter mating device of example 139 or 140 that further includes a cylinder internal to the external wall and the internal passageway is between the cylinder and the external wall.

Example 143: The catheter mating device of any of examples 127-142, wherein the distal end of the stem juxtaposed the apparatus has a durometer of 5-65 Shore A greater than the durometer of the external wall.

Example 144: The catheter mating device of any of examples 139-143, wherein when the apparatus is in its second, expanded position, it defines an opening to the internal passageway through which fluid can enter.

Example 145: The catheter mating device of any of examples 127-144 that is connected to a catheter when the apparatus is in its second, expanded position.

Further non-limiting examples are below. Unless expressly stated as depending from any of the First Set of Examples above, dependent examples below depend only from numbered examples below.

Example 1: A urinary catheter comprising:
(a) a tube, the tube having (i) a wall with an outer surface, the outer surface having a first cross-sectional area, (ii) a lumen, (iii) a distal end with one or more openings in communication with the lumen, and (iv) a proximal end with an opening in communication with the lumen;
(b) a valve that is operated to be in (i) a closed configuration, wherein fluid does not flow out of the proximal end, or (ii) an open configuration in which fluid does flow out of the proximal end: and
(c) a retainer portion between the distal end and the proximal end, the retainer portion having (i) an outer wall that has an outer surface, an inner surface, a first, compressed position in which it is configured to fit through the penile urethra, and a second, expanded position in which it has a maximum cross-sectional area at least twice as great as the first cross-sectional area and is configured to not fit through the penile urethra, (ii) a cavity inside of the outer wall, (iii) a core inside of the cavity, the core having a passage in which the tube is positioned, and (iv) at least one expansion structure positioned inside of the cavity and connected to the core, the at least one expansion structure being configured to contact an inner surface of the outer wall and exert outward force on the outer wall.

Example 2: The urinary catheter of example 1, wherein the retainer portion has a maximum cross-sectional area that is 2-3 times greater than the first cross-sectional area.

Example 3: The urinary catheter of example 1, wherein the retainer portion has a maximum cross-sectional area that is 1.5-4 times larger than the first cross-sectional area.

Example 4: The urinary catheter of example 1, wherein the maximum cross-sectional area is an area from: (24 mm)¼ to (25 mm) am, or (4 mm) am to $(25\ mm)^2\pi$.

Example 5: The urinary catheter of example 1, wherein the retainer portion is circular in cross-section at its maximum cross-sectional area, and has a diameter of 5 mm to 10 mm at the position of the maximum cross-sectional area.

Example 6: The urinary catheter of example 1, wherein the retainer portion has a hardness of an amount from: 1 to 70 Shore A, or 5-15 Shore A, or 10-70 Shore A, or 5-15 Shore A, or 10-15 Shore A.

Example 7: The urinary catheter of example 1, wherein the retainer portion is comprised of silicone.

Example 8: The urinary catheter of example 1, wherein the outer wall of the retainer portion can be physically compressed to ½ or less of the maximum cross-sectional area when subjected to a compressive force evenly applied along the outer wall of an amount from: 3-5 lbs., or 2-4 lbs., or 2-6 lbs., or 4-6 lbs., or 5-10 lbs., or 7-10 lbs., or 5-22 lbs.

Example 9: The urinary catheter of example 1, wherein the outer wall can be compressed from the second, expanded position to the first, compressed position, when the outer wall is subjected to a compressive force evenly applied along the outer wall of an amount from: 3-5 lbs., or 2-4 lbs., or 2-6 lbs., or 4-6 lbs., or 5-10 lbs., or 7-10 lbs., or 5-22 lbs.

Example 10: The urinary catheter of example 1, wherein the retainer portion is configured to have a maximum diameter of 0.3 mm to 8.0 mm when in the first, compressed position, and configured to have a maximum diameter of 4.0 mm to 15 mm when in the second, expanded position.

Example 11: The urinary catheter of example 1 that further includes one or more sensors on or in the catheter.

Example 12: The urinary catheter of example 11 that is configured such that the one or more sensors are positioned in a bladder when the urinary catheter is positioned in a lower urinary tract of a human male.

Example 13: The urinary catheter of example 11, wherein the one or more sensors are positioned at least partially in the lumen.

Example 14: The urinary catheter of example 11, wherein the one or more sensors are configured to collect data of the patient, the data comprising one or more of fluid pressure inside of the bladder, fluid volume inside of the bladder, temperature inside of the bladder, acidity of urine, bacteria level and type in urine, chemical composition of urine, motion of the patient, location of the patient, and fluid flow when emptying the bladder.

Example 15: The urinary catheter of example 1 that includes a second lumen and one or more antennas positioned in the second lumen.

Example 16: The urinary catheter of example 1 that further includes a second lumen that includes one or more of: one or more sensors, and one or more antennas.

Example 17: The urinary catheter of example 16, wherein the second lumen has a length and includes one antenna that is at least half the length of the lumen.

Example 18: The urinary catheter of example 16, wherein the second lumen has a length and includes one antenna that extends at least 90% of the length.

Example 19: The urinary catheter of example 1 that further includes an antenna that is in electrical contact with the one or more sensors.

Example 20: The urinary catheter of example 19, wherein the antenna is physically connected to the one or more sensors.

Example 21: The urinary catheter of example 11 that has a plurality of sensors.

Example 22: The urinary catheter of example 11, wherein the one or more sensors are positioned at one or more of: the distal end of the catheter, inside the lumen of the catheter, inside the second lumen of the catheter, and in or on the retainer portion.

Example 23: The urinary catheter of example 1, wherein the at least one expansion structure is wing shaped.

Example 24: The urinary catheter of example 1, wherein the retainer portion comprises two expansion structures in the cavity and each structure is configured to apply outward force on the outer cover.

Example 25: The urinary catheter of example 24, wherein each expansion structure is wing shaped.

Example 26: The urinary catheter of example 30, wherein each expansion structure is connected to and structure extends outward from the core.

Example 27: The urinary catheter of example 26, wherein each expansion structure has an intermediate section.

Example 28: The urinary catheter of example 1, wherein each expansion structure has a length that is at least 50% of the circumference of an inner wall of the outer cover.

Example 29: The urinary catheter of example 31, wherein each expansion structure has a length that is greater than 50% of the circumference of an inner wall of the outer cover.

Example 30: The urinary catheter of example 1, wherein each expansion structure has an intermediate section having a thickness that is 25% or more, or 30% or more, or 40% or more of a thickness of the outer cover.

Example 31: The urinary catheter of example 1 that further comprises an extendable flap juxtaposed the distal end, wherein the extendable flap has a first, contracted position in which it is positioned against an outer wall of the tube, and a second, extended position in which it extends outward from the outer wall of the tube.

Example 32: The urinary catheter of example 31, wherein the extendable flap is comprised of silicone.

Example 33: The urinary catheter of example 31, wherein the extendable flap has a length that is at least 30%, or at least 40%, or at least 50%, or at least 60%, or at least 70% of an outer circumference of the tube.

Example 34: The urinary catheter of example 31, wherein the extendable flap has a thickness that is at least 50%, at least 60%, at least 70%, at least 80%, at least 90%, or at least 100% of a thickness of the tube wall.

Example 35: The urinary catheter of any of examples 1-34, wherein the retention force in the forward direction after the catheter is properly positioned in the bladder of an adult male is from about 1.15 lbs. to about 1.5 lbs., or from about 1.15 lbs. to 1.70 lbs.

Example 36: The urinary catheter of any of examples 1-35, wherein the retention force in the reverse direction after the catheter is properly positioned in the bladder of an adult male, is from about 1.30 lbs. to about 2.0 lbs., or about 1.3 lbs. to about 2.0 lbs., or about 1.3 lbs. to about 1.8 lbs.

Example 37: The urinary catheter of any of examples 1-36 wherein the extendable flap has a length (as measured from the position where it connects to an outer wall of the tube to the outermost edge of the extendable flap) that is at least 20%, or at least 30%, or at least 40%, or at least 50%, or at least 60%, or at least 70%, or at least 80%, or at least 90%, or at least 100%, or at least 120%, or at least 150%, or any amount from 20% to 150% of the outer circumference of the tube.

Example 38: The urinary catheter of any of examples 1-37, wherein the extendable flap has a thickness that is at least 10%, at least 20%, at least 30%, at least 40°/o, at least 50%, at least 60%, at least 70%, at least 80%, at least 90%, at least 100%, at least 110%, at least 120%, at least 130%, at least 1540%, at least 150%, or any amount from 10% to 150% of the thickness of the tube wall.

Example 39: The urinary catheter of any of examples 1-38, wherein the extendable flap has a 70A shore hardness.

Example 40: The urinary catheter of any of examples 1-39, wherein the extendable flap has a 0.6 mm wall thickness.

Example 41: The urinary catheter of any of examples 37-40, wherein the extendable flap has an axial length that is about equal to the length, or any amount from about 50% of the length to about 200% of the length, such as at least 10%, at least 20%, at least 30%, at least 40%, at least 50%, at least 60%, at least 70%, at least 80%, at least 90%, at least 100%, at least 110%, at least 120%, at least 130%, at least 1540%, at least 150% at least 160%, at least 170%, at least 180%, at least 190%, or at least 200%.

Example 42: The urinary catheter of any of examples 1-41, wherein the extendable flap comprises an edge that is thicker than the thickness at the center of the flap.

Example 43: The urinary catheter of example 42, wherein the edge thickness is any amount from 10% to 100%, such as 10%, 20%, 30%, 40%, 50%, 60%, 70%, 80%, 90%, or 100% of the thickness of the center.

Example 44: The urinary catheter of any of examples 1-43, wherein the extendable flap is attached to the tube and has a body portion that surrounds the tube.

Example 45: The urinary catheter of any of examples 1-30 that further comprises an dual extendable flap on the distal end, wherein the dual extendable flap has a first flap, a second flap, a first, contracted position in which the first flap and the second flap are positioned against an outer wall of the tube, and a second, extended position in which the first flap and the second flap extend outward from the outer wall of the tube.

Example 46: The urinary catheter of example 45, wherein the dual extendable flap is comprised of silicone.

Example 47: The urinary catheter of example 45, wherein the first flap and the second flap each has a length that is at least 30%, or at least 40%, or at least 50%, or at least 60%, or at least 70% of an outer circumference of the tube.

Example 48: The urinary catheter of example 45, wherein the first flap and the second flap each has a thickness that is at least 50%, at least 60%, at least 70%, at least 80%, at least 90%, or at least 100% of a thickness of the tube wall.

Example 49: The urinary catheter of any of examples 45-48, wherein the retention force in the forward direction after the catheter is properly positioned in the bladder of an adult male is from about 1.15 lbs. to about 1.5 lbs., or from about 1.15 lbs. to 1.70 lbs.

Example 50: The urinary catheter of any of examples 45-49, wherein the retention force in the reverse direction after the catheter is properly positioned in the bladder of an adult male, is from about 1.30 lbs. to about 2.0 lbs., or about 1.3 lbs. to about 2.0 lbs., or about 1.3 lbs. to about 1.8 lbs.

Example 51: The urinary catheter of any of examples 45-50, wherein the first flap and the second flap each has a length that is at least 20%, or at least 30%, or at least 40%, or at least 50%, or at least 60%, or at least 70%, or at least 80%, or at least 90', or at least 100%, or at least 120%, or at least 150%, or any amount from 20% to 150% of the outer circumference of the tube.

Example 52: The urinary catheter of any of examples 45-51, wherein the first flap and the second flap each has a thickness that is at least 10%, at least 20%, at least 30%, at least 40%, at least 50%, at least 60%, at least 70%, at least 80%, at least 90%, at least 100%, at least 110%, at least 120%, at least 130%, at least 1540%, at least 150%, or any amount from 10% to 150% of the thickness of the tube.

Example 53: The urinary catheter of any of examples 45-52, wherein the dual extendable flap has a 70A shore hardness.

Example 54: The urinary catheter of any of examples 45-53, wherein the first flap and the second flap each has an axial length that is about equal to the length, or any amount from about 50% of the length to about 200% of the length, such as at least 10%, at least 20%, at least 30%, at least 40%, at least 50%, at least 60%, at least 70%, at least 80%, at least 90%, at least 100%, at least 110%, at least 120%, at least 130%, at least 1540%, at least 150% at least 160%, at least 170%, at least 180%, at least 190%, or at least 200%.

Example 55: The urinary catheter of any of examples 45-54, wherein the first flap and the second flap each has an edge that is thicker than the thickness at the center of the flap.

Example 56: The urinary catheter of example 55, wherein first flap and the second flap each has a thickness that is any amount from 10% to 100%, such as 10%, 20%, 30%, 40%, 50%, 60%, 70%, 80%, 90%, or 100%.

Example 57: The urinary catheter of any of examples 45-56, wherein the dual extendable flap is attached to the tube and has a body portion that surrounds the tube.

Example 58: The urinary catheter of any of examples 45-57, wherein the first flap and the second flap each has a bulb at its tip.

Example 59: The urinary catheter of example 58, wherein each bulb is circular in cross section.

Example 60: The urinary catheter of example 59, wherein each bulb has a diameter that is greater than the thickness the center of the first flap and the second flap.

Example 61: The urinary catheter of example 60, wherein each bulb has a diameter that is from 10% to 200% greater than the thickness of the center.

Example 62: The urinary catheter of example 60, wherein each bulb has a diameter that is greater than the thickness of the center of the first flap and greater than the thickness of the center of the second flap by at least: 10%, 20%, 30%, 40%, 50%, 60%, 70%, 80%, 90%, 100%, 100%, 120%, 130%, 140%, 150%, 160%, 170%, 180%, 190%, or 200%.

Example 63: The catheter system of First Set of Examples 1-65 or the urinary catheter of examples 1-62, wherein the at least one expansion structure is connected to the core.

Example 64: The catheter mating device of any of the First Set of Examples 131-145, wherein each of the tips has a semi-circular cross section.

Example 65: The catheter mating device of any of the First Set of Examples 131-145, wherein each of the tips has a conical outer profile.

Example 66: The catheter mating device of example 65, wherein each tip has a lower ridge.

Example 67: The catheter mating device of example 66, wherein each tip is narrower at its distal end than at the lower ridge.

Example 68: The catheter mating device of example 67, wherein the distal end is at least 30% narrower than the lower ridge.

Example 69: The catheter mating system of any of examples 64-68 or any of the First Set of Examples 127-145, wherein the apparatus comprises two sections and each section has a first end that is received inside of the distal end of the stem and that comprises a protrusion, and the distal end of the stem has two openings, wherein each protrusion is received in one of the two openings in order to connect the section to the stem.

Example 70: A system comprising the urinary catheter of any of examples 1-62 and the catheter mating device of any of the First Set of Examples 127-145.

Example 71: The system of example 70, wherein the urinary catheter is connected to the catheter mating device.

Example 72: The catheter of any of the First Set of Examples 66-93 that further includes an extendable flap juxtaposed the distal end, wherein the extendable flap has a first, contracted position in which it is positioned against an outer wall of the tube, and a second, extended position in which it extends outward from the outer wall of the tube.

Example 73: The catheter of example 72, wherein the extendable flap is comprised of silicone.

Example 74: The catheter of example 72, wherein the extendable flap has a length that is at least 30%, or at least 40%, or at least 50%, or at least 60%, or at least 70% of an outer circumference of the tube.

Example 75: The catheter of example 72, wherein the extendable flap has a thickness that is at least 50%, at least 60%, at least 70%, at least 80%, at least 90%, or at least 100% of a thickness of the tube wall.

Example 76: The catheter of any of examples 72-75 wherein the extendable flap has a length (as measured from the position where it connects to an outer wall of the tube to the outermost edge of the extendable flap) that is at least 20%, or at least 30%, or at least 40%, or at least 50%, or at least 60%, or at least 70%, or at least 80%, or at least 90%, or at least 100%, or at least 120%, or at least 150%, or any amount from 20% to 150% of the outer circumference of the tube.

Example 77: The catheter of any of examples 72-76, wherein the extendable flap has a thickness that is at least 10%, at least 20%, at least 30%, at least 40%, at least 50%, at least 60%, at least 70%, at least 80%, at least 90%, at least 100%, at least 110%, at least 120%, at least 130%, at least 1540%, at least 150%, or any amount from 10% to 150% of the thickness of the tube wall.

Example 78: The catheter of any of examples 72-77, wherein the extendable flap has a 70A shore hardness.

Example 79: The catheter of any of examples 72-78, wherein the extendable flap has a 0.6 mm wall thickness.

Example 80: The catheter of any of examples 76-79, wherein the extendable flap has an axial length that is about equal to the length, or any amount from about 50% of the length to about 200% of the length, such as at least 10%, at least 20%, at least 30%, at least 40%, at least 50%, at least 60%, at least 70%, at least 80%, at least 90%, at least 100%, at least 110%, at least 120%, at least 130%, at least 1540%, at least 150% at least 160%, at least 170%, at least 180%, at least 190%, or at least 200%.

Example 81: The catheter of any of examples 72-80, wherein the extendable flap comprises an edge that is thicker than the thickness at the center of the flap.

Example 82: The catheter of example 81, wherein the edge thickness is any amount from 10% to 100%, such as 10%, 20%, 30%, 40%, 50%, 60%, 70%, 80%, 90%, or 100% of the thickness of the center.

Example 83: The catheter of any of examples 72-82, wherein the extendable flap is attached to the tube and has a body portion that surrounds the tube.

Example 84: The catheter of any of First Set of Examples 66-93 that further comprises an dual extendable flap on the distal end, wherein the dual extendable flap has a first flap, a second flap, a first, contracted position in which the first flap and the second flap are positioned against an outer wall of the tube, and a second, extended position in which the first flap and the second flap extend outward from the outer wall of the tube.

Example 85: The catheter of example 84, wherein the dual extendable flap is comprised of silicone.

Example 86: The catheter of example 84, wherein the first flap and the second flap each has a length that is at least 30%, or at least 40%, or at least 50%, or at least 60%, or at least 70% of an outer circumference of the tube.

Example 87: The catheter of example 84, wherein the first flap and the second flap each has a thickness that is at least 50%, at least 60%, at least 70%, at least 80%, at least 90%, or at least 100% of a thickness of the tube wall.

Example 88: The catheter of any of examples 84-87, wherein the retention force in the forward direction after the catheter is properly positioned in the bladder of an adult male is from about 1.15 lbs. to about 1.5 lbs., or from about 1.15 lbs. to 1.70 lbs.

Example 89: The catheter of any of examples 84-88, wherein the retention force in the reverse direction after the catheter is properly positioned in the bladder of an adult male, is from about 1.30 lbs. to about 2.0 lbs., or about 1.3 lbs. to about 2.0 lbs., or about 1.3 lbs. to about 1.8 lbs.

Example 90: The catheter of any of examples 84-89, wherein the first flap and the second flap each has a length that is at least 20%, or at least 30%, or at least 40%, or at least 50%, or at least 60%, or at least 70%, or at least 80%, or at least 90%, or at least 100%, or at least 120%, or at least 150%, or any amount from 20% to 150% of the outer circumference of the tube.

Example 91: The catheter of any of examples 84-90, wherein the first flap and the second flap each has a thickness that is at least 10%, at least 20%, at least 30%, at least 40%, at least 50%, at least 60%, at least 70%, at least 80%, at least 90%, at least 100%, at least 110%, at least 120%, at least 130%, at least 1540%, at least 150%, or any amount from 10% to 150% of the thickness of the tube.

Example 92: The catheter of any of examples 84-91, wherein the dual extendable flap has a 70A shore hardness.

Example 93: The catheter of any of examples 84-92, wherein the first flap and the second flap each has an axial length that is about equal to the length, or any amount from about 50% of the length to about 200% of the length, such as at least 10%, at least 20%, at least 30%, at least 40%, at least 50%, at least 60%, at least 70%, at least 80%, at least 90%, at least 100°i°, at least 110%, at least 120%, at least 130%, at least 1540%, at least 150% at least 160%, at least 170%, at least 180%, at least 190%, or at least 200%.

Example 94: The catheter of any of examples 84-93, wherein the first flap and the second flap each has an edge that is thicker than the thickness at the center of the flap.

Example 95: The catheter of example 94, wherein first flap and the second flap each has a thickness that is any amount from 10% to 100%, such as 10%, 20%. 30%, 40%, 50%, 60%, 70%, 80%, 90%, or 100%.

Example 96: The catheter of any of examples 84-95, wherein the dual extendable flap is attached to the tube and has a body portion that surrounds the tube.

Example 97: The catheter of any of examples 84-96, wherein the first flap and the second flap each has a bulb at its tip.

Example 98: The catheter of example 97, wherein each bulb is circular in cross section.

Example 99: The catheter of example 98, wherein each bulb has a diameter that is greater than the thickness the center of the first flap and the second flap.

Example 100: The catheter of example 99, wherein each bulb has a diameter that is from 10% to 200% greater than the thickness of the center.

Example 101: The catheter of example 100, wherein each bulb has a diameter that is greater than the thickness of the center of the first flap and the center of the second flap by at least: 10%, 20%, 30%, 40%, 50%, 60%, 70%, 80%, 90%, 100%, 100%, 120%, 130%, 140%, 150%, 160%, 170%, 180%, 190%, or 200%.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result. No language in the specification should be construed as indicating that any non-claimed limitation is included in a claim. The terms "a" and "an" expressly used in the context of describing the invention (especially in the context of the following claims) are to be construed to cover both the singular and the plural, unless otherwise indicated herein or clearly contradicted by context.

What is claimed is:

1. A urinary catheter comprising:
   (a) a tube, the tube having (i) a wall with an outer surface, the outer surface having a first cross-sectional area, (ii) a lumen, (iii) a distal end with one or more openings in communication with the lumen, and (iv) a proximal end with an opening in communication with the lumen;
   (b) a valve that is operated to be in (i) a closed configuration, wherein fluid does not flow out of the proximal end, or (ii) an open configuration in which fluid does flow out of the proximal end; and (c) a retainer portion between the distal end and the proximal end, wherein the retainer portion has (i) an outer wall that has an outer surface and an inner surface, (ii) a cavity inside of the outer wall, (iii) a core inside of the cavity, the core having a passage in which the tube is positioned, and (iv) at least one expansion structure positioned inside of the cavity, wherein the at least one expansion structure has a first end connected to the core, a second end in contact with the inner surface of the outer wall of the retainer portion, and an intermediate section between the first end and the second end and in contact with the inner surface of the outer wall of the retainer portion so as to apply outward pressure to the outer wall, wherein the intermediate section and the outer wall are configured to be compressed to a compressed position when compressive force is applied by a wall of a penile urethral, and when in the compressed position are configured to fit through the penile urethra, and the intermediate section and outer wall are configured to expand to an expanded position when compressive force is not applied by the wall of the penile urethra, and when in the expanded position the outer wall has a diameter that is at least twice as its diameter when positioned in the penile urethra.

2. The urinary catheter of claim 1, wherein a maximum cross-sectional area of the retainer portion is 2-3 times greater than the first cross-sectional area.

3. The urinary catheter of claim 1, Wherein a maximum cross-sectional area of the retainer portion is 1.5-4 times larger than the first cross-sectional area.

4. The urinary catheter of claim 1, wherein a maximum cross-sectional area of the retainer portion is an area from: $(24\ mm^2\pi$ to $(25\ mm)^2\pi$, or $(4\ mm)^2\pi$ to $(25\ mm)^2\pi$.

5. The urinary catheter of claim 1, wherein the retainer portion is circular in cross-section at its maximum cross-sectional area, and has a diameter of 5 mm to 10 mm at the position of the maximum cross-sectional area.

6. The urinary catheter of claim 1, wherein the retainer portion has a hardness of an amount from: 1 to 70 Shore A, or 5-15 Shore A, or 10-20 Shore A, or 5-15 Shore A, or 10-15 Shore A.

7. The urinary catheter of claim 1, wherein the retainer portion is comprised of silicone.

8. The urinary catheter of claim 1, wherein the outer wall of the retainer portion can be physically compressed to ½ or less of the maximum cross-sectional area when subjected to a compressive force evenly applied along the outer wall of an amount from: 3-5 lbs.: or 2-4 lbs., or 1-6 lbs., or 4-6 lbs., or 5-10 lbs., or 7-10 lbs., or 5-22 lbs.

9. The urinary catheter of claim 1, wherein the outer wall can be compressed from the second, expanded position to the first, compressed position, when the outer wall is subjected to a compressive force evenly applied along the outer wall of an amount from 3-5 lbs.: or 2-4 lbs., or 1-6 lbs., or 4-6 lbs., or 5-10 lbs., or 7-10 lbs., or 5-22 lbs.

10. The urinary catheter of claim 1, wherein the retainer portion is configured to have a maximum diameter of 0.3 mm to 8.0 mm when in the first, compressed position, and configured to have a maximum diameter of 4.0 mm to 15 mm when in the second, expanded position.

11. The urinary catheter of claim 1 that further includes one or more sensors on or in the catheter.

12. The urinary catheter of claim 11 that is configured such that the one or more sensors are positioned in a bladder when the urinary catheter is positioned in a lower urinary tract of a human male.

13. The urinary catheter of claim 11, wherein the one or more sensors are positioned at least partially in the lumen.

14. The urinary catheter of claim 11, wherein the one or more sensors are s configured to collect data of a patient, the data comprising one or more of: fluid pressure inside of the bladder, fluid volume inside of the bladder, temperature inside of the bladder, acidity of urine, bacteria level and type in urine, chemical composition of urine, motion of the patient, location of the patient, and fluid flow when emptying the bladder.

15. The urinary catheter of claim 11 that further includes an antenna that is in electrical contact with the one or more sensors.

16. The urinary catheter of claim 1 that includes a second lumen and one or more antennas positioned in the second lumen.

17. The urinary catheter of claim 1 that further includes a second lumen that includes at least one sensor and at least one antenna.

18. The urinary catheter of claim 1, wherein each expansion structure has a length that is at least 50% of a circumference of the inner watt surface of the outer wall.

19. The urinary catheter of claim 1, wherein each expansion structure has a length that is greater than 50% of a circumference of the inner surface of the outer wall.

20. The urinary catheter of claim 1, wherein each expansion structure has an intermediate section having a thickness that is 25% or more, or 30% or more, or 40% or more of a thickness of the outer wall.

21. The urinary catheter of claim 1 that further comprises an extendable flap on the distal end, wherein the extendable flap has a first, contracted position in which the extendable flap is positioned against the outer surface of the tube, and a second, extended position in which the extendable flap extends outward from the outer wall of the tube.

22. The urinary catheter of claim 21, wherein the extendable flap has a first side connected to the tube and a second side opposite the first side and a length measured between the first side and the second side, wherein the length is at least 30%, or at least 40%, or at least 50%, or at least 60%, or at least 70% of an outer circumference of the tube.

23. The urinary catheter of claim 21, wherein an intermediate section of the extendable flap has a thickness that is at least 50%, at least 60%, at least 70%, at least 80%, at least 90%, or at least 100% of a thickness of the tube wall.

24. The urinary catheter of claim 1 that further comprises a dual extendable flap positioned at the distal end, wherein the dual extendable flap has a first flap, a second flap, a first, contracted position in which the first flap and the second flap are each positioned against the outer surface of the tube wall, and a second, extended position in which the first flap and the second flap each extend outward from the outer surface of the tube wall.

25. The urinary catheter of claim 1 that further comprises an extendable flap juxtaposed the distal end, wherein a length of the extendable flap is at least 30%, or at least 40%, or at least 50%, or at least 60%, or at least 70% of a circumference of the outer surface of the tube.

26. The urinary catheter of claim 25, wherein the extendable flap has a thickness that is at least 50%, at least 60%, at least 70%, at least 80%, at least 90%, or at least 100% of a thickness of the tube wall, and wherein a first side of the extendable flap has an axial length as measured along the tube, wherein the axial length is about equal to the length of the extendable flap, or any amount from about 50% of the length to about 200% of the length of the extendable flap.

27. The urinary catheter of claim 24, wherein the first flap and the second flap each has a thickness that is at least 50%, at least 60%, at least 70%, at least 80%, at least 90%, or at least 100% of a thickness of the tube wall, and wherein the first flap has a first side connected to the tube and a second side opposite the first side, and second flap has a first side connected to the tube and a second side opposite the first side, and the first flap and the second flap each has a length as measured between the first side and the second side, wherein the length is at least 30%, or at least 40%, or at least 50%, or at least 60%, or at least 70% of a circumference of the outer surface of the tube.

28. The urinary catheter of claim 24, wherein the first flap and the second flap each has a bulb at its second end, wherein each bulb has a diameter that is from 10% to 200% greater than the thickness of the intermediate section.

29. The urinary catheter of claim 1, wherein a retention force in a forward direction in order to move the urinary catheter after it is properly positioned in the bladder of an adult male is from about 1.15 lbs. to about 1.5 lbs., or from about 1.15 lbs. to 1.70 lbs., and a retention force in a reverse direction in order to move the urinary catheter after it is properly positioned in the bladder of an adult male is from about 1.30 lbs. to about 2.0 lbs., or about 1.3 lbs to about 2.0 lbs., or about 1.3 lbs. to about 1.8 lbs.

30. The urinary catheter of claim 1, wherein the at least one expansion structure comprises two expansion structures and each of the two expansion structures has a first end juxtaposed the outer surface of the tube, a second end in contact with the inner surface of the retainer portion, and an intermediate section that touches the inner surface of the retainer portion and that is configured to apply outward force to urge the outer wall to the second, expanded position.

31. The urinary catheter of claim 30, wherein each of the two expansion structures has a length as measured from the first end to the second end, and the length is at least 50% of the circumference of the inner wall of the outer cover, and the intermediate section has a thickness that is 25% or more, or 30% or more, or 40% or more of a thickness of the outer cover.

32. The urinary catheter of claim 1, wherein the at least one expansion structure has a length as measured from the first end to the second end, and the length is at least 50% of the circumference of the inner surface of the outer wall, and the intermediate structure has a thickness that is 25% or more, or 30% or more, or 40% or more of a thickness of the outer cover.

\* \* \* \* \*